(12) United States Patent
Sasikumar et al.

(10) Patent No.: US 12,187,689 B2
(45) Date of Patent: *Jan. 7, 2025

(54) CRYSTALLINE FORMS OF 3-SUBSTITUTED 1,2,4-OXADIAZOLE

(71) Applicant: Aurigene Oncology Limited, Bangalore (IN)

(72) Inventors: Pottayil Govindan N. Sasikumar, Bangalore (IN); Seetharamaiah Setty S. Naremaddepalli, Bangalore (IN)

(73) Assignee: Aurigene Oncology Limited, Bangalore (IN)

( * ) Notice: Subject to any disclaimer, the term of this patent is extended or adjusted under 35 U.S.C. 154(b) by 0 days.

This patent is subject to a terminal disclaimer.

(21) Appl. No.: 18/197,414

(22) Filed: May 15, 2023

(65) Prior Publication Data

US 2023/0278970 A1  Sep. 7, 2023

Related U.S. Application Data

(63) Continuation of application No. 17/461,512, filed on Aug. 30, 2021, now Pat. No. 11,680,051, which is a continuation of application No. 16/755,439, filed as application No. PCT/IB2018/057840 on Oct. 10, 2018, now Pat. No. 11,136,300.

(30) Foreign Application Priority Data

Oct. 11, 2017 (IN) .............................. 201741036169

(51) Int. Cl.
C07D 271/06 (2006.01)

(52) U.S. Cl.
CPC ........ C07D 271/06 (2013.01); C07B 2200/13 (2013.01)

(58) Field of Classification Search
CPC .................................................. C07D 271/06
See application file for complete search history.

(56) References Cited

U.S. PATENT DOCUMENTS

| | | | |
|---|---|---|---|
| 3,227,725 A | 1/1966 | Fernand et al. |
| 5,387,585 A | 2/1995 | Borer et al. |
| 5,665,718 A | 9/1997 | Godel et al. |
| 8,735,553 B1 | 5/2014 | Li et al. |
| 9,771,338 B2 | 9/2017 | Sasikumar et al. |
| 10,173,989 B2 | 1/2019 | Sasikumar et al. |
| 10,590,093 B2 | 3/2020 | Sasikumar et al. |
| 10,781,189 B2 | 9/2020 | Sasikumar et al. |
| 10,961,205 B2 | 3/2021 | Sasikumar et al. |
| 11,040,948 B2 | 6/2021 | Yu |
| 11,136,300 B2 | 10/2021 | Sasikumar et al. |
| 11,465,976 B2 | 10/2022 | Sasikumar et al. |
| 11,497,734 B2 | 11/2022 | Sasikumar et al. |
| 11,497,735 B2 | 11/2022 | Sasikumar et al. |
| 11,643,401 B2 | 5/2023 | Yu |
| 11,680,051 B2 | 6/2023 | Sasikumar et al. |
| 2005/0272779 A1 | 12/2005 | Edwards et al. |
| 2007/0197522 A1 | 8/2007 | Edwards et al. |
| 2007/0225332 A1 | 9/2007 | Gu et al. |
| 2009/0099227 A1 | 4/2009 | Fyfe et al. |
| 2011/0275673 A1 | 11/2011 | Xiang et al. |
| 2013/0022629 A1 | 1/2013 | Sharpe et al. |
| 2014/0199334 A1 | 7/2014 | Sasikumar et al. |
| 2014/0235620 A1 | 8/2014 | Caferro et al. |
| 2015/0073024 A1 | 3/2015 | Sasikumar et al. |
| 2015/0073042 A1 | 3/2015 | Sasikumar et al. |
| 2018/0044303 A1 | 2/2018 | Sasikumar et al. |
| 2020/0061030 A1 | 2/2020 | Sasikumar et al. |
| 2020/0239422 A1 | 7/2020 | Sasikumar et al. |
| 2020/0247766 A1 | 8/2020 | Yu |
| 2020/0289477 A1 | 9/2020 | Sasikumar et al. |
| 2020/0368210 A1 | 11/2020 | Sasikumar et al. |
| 2021/0380544 A1 | 12/2021 | Yu |
| 2022/0048875 A1 | 2/2022 | Sasikumar et al. |
| 2023/0062570 A1 | 3/2023 | Sasikumar et al. |
| 2023/0081191 A1 | 3/2023 | Govindan et al. |
| 2023/0110077 A1 | 4/2023 | Sasikumar et al. |
| 2023/0167076 A1 | 6/2023 | Sasikumar et al. |
| 2023/0167077 A1 | 6/2023 | Yu |

FOREIGN PATENT DOCUMENTS

| | | | |
|---|---|---|---|
| CN | 105814028 A | 7/2016 |
| CN | 111163772 A | 5/2020 |
| JP | 2016/532710 A | 10/2016 |
| JP | 2016/539662 A | 12/2016 |
| JP | 2021/501127 A | 1/2021 |
| KR | 20160081897 A | 7/2016 |
| WO | WO-2001/014557 A1 | 3/2001 |
| WO | WO-2002/079499 A1 | 10/2002 |
| WO | WO-2002/086083 A2 | 10/2002 |
| WO | WO-2003/042402 A2 | 5/2003 |
| WO | WO-03/070711 A1 | 8/2003 |

(Continued)

OTHER PUBLICATIONS

U.S. Appl. No. 17/962,096, Pending.
U.S. Appl. No. 18/101,387, Pending.
Anderson et al., "Lag-3, Tim-3, and TIGIT: Co-inhibitory Receptors with Specialized Functions in Immune Regulation," Immunity, 44(5): 989-1004 (2016).
Ardestani et al., "Cell death features induced in Leishmania major by 1,3,4-thiadiazole derivatives," Exp Parasitol, 132(2): 116-122 (2012).
Ashizawa., "Physico-chemical studies on the molecular details of drug crystals" Pharm Tech Japan, vol. 18, No. 10 (2002).
Berge et al., "Pharmaceutical Salts," Journal of Pharmaceutical Sciences, 66(1):1-19 (1977).
Booher et al., "Combination of IRAK4 Inhibitor CA-4948 with BCL2 Inhibitor Venetoclax Induces Tumor Regression in an ABC-DLBCL Xenograft Model", Blood, 130(1): 1534, (2017).

(Continued)

*Primary Examiner* — Shawquia Jackson
(74) *Attorney, Agent, or Firm* — Foley Hoag LLP; David P. Halstead; Alexander J. Chatterley

(57) ABSTRACT

The invention relates to crystalline forms of a 3-substituted 1,2,4-oxadiazole compound, methods of their preparation, and related pharmaceutical preparations thereof. The invention also relates to preparations suitable for pharmaceutical, veterinary, and agriculturally-relevant uses.

32 Claims, 5 Drawing Sheets

(56) References Cited

FOREIGN PATENT DOCUMENTS

| WO | WO-2004/004771 A1 | 1/2004 |
|---|---|---|
| WO | WO-2004/056875 A1 | 7/2004 |
| WO | WO-2005/056550 A2 | 6/2005 |
| WO | WO-2006/121168 A1 | 11/2006 |
| WO | WO-2006/133216 A2 | 12/2006 |
| WO | WO-2007/075749 A2 | 7/2007 |
| WO | WO-2008/011557 A2 | 1/2008 |
| WO | WO-2008/039431 A2 | 4/2008 |
| WO | WO-2008/156712 A1 | 12/2008 |
| WO | WO-2009/006555 A2 | 1/2009 |
| WO | WO-2009/059162 A1 | 5/2009 |
| WO | WO-2009/105712 A1 | 8/2009 |
| WO | WO-2010/051447 A1 | 5/2010 |
| WO | WO-2010/077634 A1 | 7/2010 |
| WO | WO-2011/066389 A1 | 6/2011 |
| WO | WO-2011/082400 A2 | 7/2011 |
| WO | WO-2011/137587 A1 | 11/2011 |
| WO | WO-2011/161699 A2 | 12/2011 |
| WO | WO-2012/129564 A2 | 9/2012 |
| WO | WO-2012/168944 A1 | 12/2012 |
| WO | WO-2013/132317 A1 | 9/2013 |
| WO | WO-2013/144704 A1 | 10/2013 |
| WO | WO-2014/055897 A2 | 4/2014 |
| WO | WO-2014/059173 A2 | 4/2014 |
| WO | WO-2014/100079 A1 | 6/2014 |
| WO | WO-2014/110298 A1 | 7/2014 |
| WO | WO-2014/141104 A1 | 9/2014 |
| WO | WO-2014/147586 A1 | 9/2014 |
| WO | WO-2015/033299 A1 | 3/2015 |
| WO | WO-2015/033301 A1 | 3/2015 |
| WO | WO-2016073470 A1 | 5/2016 |
| WO | WO-2016/142833 A1 | 9/2016 |
| WO | WO-2016/142852 A1 | 9/2016 |
| WO | WO-2016/142886 A2 | 9/2016 |
| WO | WO-2017/055860 A1 | 4/2017 |
| WO | WO-2017/079116 A2 | 5/2017 |
| WO | WO-2018/047143 A1 | 3/2018 |
| WO | WO-2018/051254 A1 | 3/2018 |
| WO | WO-2018/073754 A1 | 4/2018 |
| WO | WO-2019/067678 A1 | 4/2019 |
| WO | WO-2019/087087 A1 | 5/2019 |
| WO | WO-2019/087092 A1 | 5/2019 |

OTHER PUBLICATIONS

Borg et al., "1,2,4-Oxadiazole Derivatives of Phenylalnine: Potential Inhibitors of Substance P Endopeptidase," Eur. J. Med. Chem., 28(10):801-810 (1993).
Brittain. "Polymorphism in pharmaceutical solids," edited by H.G Brittain, D.J.W. Grant (chapter 1) p. 1-10 and J.K. Guillory (Chapter 5) p. 183-226 (1999).
Byrn et al., "Pharmaceutical Solids: A Strategic Approach to Regulatory Considerations," Pharmaceutical Research, 12(7):945-954 (1995).
CAS Registry No. 1252104-30-5 (2013).
CAS Registry No. 1356744-17-6 (2012).
CAS Registry No. 146429-76-5 (2013).
CAS Registry No. 1494629-78-5 (2013).
CAS Registry No. 1496514-97-6 (2013).
CAS Registry No. 1496518-51-4 (2013).
CAS Registry No. 1557852-63-7 (2014).
CAS Registry No. 1848907-06-1 (2016).
CAS Registry No. 1848909-97-6 (2016).
CAS Registry No. 1857027-85-0 (2016).
CAS Registry No. 1868314-35-5 (2016).
CAS Registry No. 1868388-36-6 (2016).
CAS Registry No. 1868393-26-3 (2016).
CAS Registry No. 1869758-25-7 (2016).
CAS Registry No. 1870159-31-1 (2016).
CAS Registry No. 1875311-16-2 (2016).
CAS Registry No. 1875758-09-0 (2016).
CAS Registry No. 1878569-90-4 (2016).
CAS Registry No. 876710-85-9 (2006).
Censi et al., "Polymorph Impact on the Bioavailability and Stability of Poorly Soluble Drugs," Molecules, 20(10): 18759-18776 (2015).
Clinical Trial NCT 02812875., "A Study of CA-170 (Oral PD-L1, PD-L2 and VISTA Checkpoint Antagonist) in Patients With Advanced Tumors and Lymphomas," U.S. National Library of Medicine: 7 pages (2016).
Clinical Trial NCT02671955., "A Study of Safety, Pharmacokinetics, Pharmacodynamics of JNJ-61610588 in Participants With Advanced Cancer," U.S. National Library of Medicine: 9 pages (2016).
Database Registry Chemical Abstracts, STN Accession No. 172410-37-6.
Database Registry Chemical Abstracts, STN Accession No. 197083-27-5.
Dempke et al., "Second-and third-generation drugs for immuno-oncology treatment—The more the better?" Eur J Cancer, 74: 55-72 (2017).
Deng et al., "A New VISTA on combination therapy for negative checkpoint regulator blockade" Journal for Immunotherapy of Cancer, 4(86): 1-7 (2016).
Extended European Search Report for EP Application No. 16761169.8 mailed Jul. 2, 2019.
Extended European Search Report for EP Application No. 16761184 mailed Jun. 26, 2018.
Extended European Search Report for EP Application No. 17862427.6 dated Jun. 5, 2020.
Extended European Search Report for EP Application No. 21209727.3 dated May 18, 2022.
Extended European Search Report for EP Application No. EP/US18/18863750 mailed May 31, 2021.
Extended European Search Report for European Application No. 18162983.3 dated Jun. 27, 2016.
Graham, "Clinical Trials of HIV Vaccines," HIV Molecular Immunology Database 2000. Edited by: Korber BT, Brander C, Haynes BF, Koup R, Kuiken C, Moore JP, Walker BD, and Watkins D. Published by: Theoretical Biology and Biophysics Group, Los Alamos National Laboratory, Los Alamos, NM, pp. 1-20-38.
Guo et al., "Design of oxobenzimidazoles and oxindoles as novel androgen receptor antagonists," Bioorg Med Chem Letts 22(7):2572-2578 (2012).
Harvey, "Immunologic and Clinical Effects of Targeting PD-1 in Lung Cancer," Nature, 96: 214-223 (2014).
Hirayama "Handbook for preparation of crystal of organic compound", Maruzen Co., Ltd 17-23, 37-40, 45-51, 57-65 (2008).
International Preliminary Report on Patentability for International Application No. PCT/IB2018/058526 mailed May 14, 2020.
International Search Report and Written Opinion for International Application No. PCT/CN2017/104485 dated Jun. 29, 2018.
International Search Report and Written Opinion for International Application No. PCT/IB2014/064279 mailed Dec. 12, 2014.
International Search Report and Written Opinion for International Application No. PCT/IB2016/051266 mailed Jul. 8, 2016.
International Search Report and Written Opinion for International Application No. PCT/IB2016/051343 mailed Jul. 28, 2016.
International Search Report and Written Opinion for International Application No. PCT/IB2017/056462 dated Jan. 10, 2018.
International Search Report and Written Opinion for International Application No. PCT/US2018/053052 dated Jan. 29, 2019.
Jin, "Role of PD-1 in Regulating T-Cell Immunity," Current Topics in Microbiology and Immunology, 350: 17-37 (2010).
Lazorchak et al., "Abstract A36: CA-170, an oral small molecule PD-L1 and VISTA immune checkpoint antagonist, promotes T cell immune activation and inhibits tumor growth in pre-clinical models of cancer," Cancer Immunology Research, 5(S3):A36 (2017).
Lee, "A practical guide to pharmaceutical polymorph screening & selection," Asian J Pharm Sci, 9(4): 163-175 (2014).
Liu et al., "Immune-checkpoint proteins VISTA and PD-1 nonredundantly regulate murine T-cell responses," PNAS, 112(21): 6682-6687 (2015).
Luo et al., "Principles of Cancer Therapy: Oncogene and Non-oncogene Addiction," Cell, 136(5): 823-837 (2009).

(56) References Cited

OTHER PUBLICATIONS

Marechal et al., "1,2,4-oxadiazoles identified by virtual screening and their non-covalent inhibition of the human 20S proteasome," Curr Med Chem 20(18):2351-2362 (2013).

Melero, "Evolving Synergistic Combinations of Targeted Immunotherapies to Combat Cancer", Nature Reviews Cancer 15:457-472 (2015).

Moussebois et al., "Synthese de Deux Nouveaux Acides Amines Phenoliques Comportant un Cycle 1,2,4-Oxadiazole," Helv. Chim. ACTA, 60(1):237-242 (1977).

Newman, "Specialized Solid Form Screening Techniques," Org Process Res Dev, 13(3): 457-471 (2012).

Ozcan et al., "Oxadiazole-Isopropylamieds as Potent and Noncovalent Proteasome Inhibitors," J. Med. Chem., 56(10):3783-3805 (2013).

Palazzo et al., "1,2,4-Oxadiazoles—IV. Synthesis and Pharmacological Properties of a Series of Substituted Aminoalkyl-1,2,4-Oxadiazoles," J. Med. Chem., 351-367 (1961).

Patwardhan et al., "Structure-Activity Relationship Studies and in Vivo Activity of Guanidine-Based Sphingosine Kinase Inhibitors: Discovery of SphK1- and SphK2-Selective Inhibitors," J. Med. Chem., 58(4):1879-1899 (2015).

Pedoeem et al., "Programmed Death-1 Pathway in Cancer and Autoimmunity," Clinical Immunology, 153: 145-152 (2014).

Rabadi et al., ""The role of VISTA in the tumor microenvironment"" Journal of Cancer Metastasis and Treatment, 8(24): 1-14 (2022).

Rietz et al., "Fragment-Based Discovery of Small Molecules Bound to T-Cell Immunoglobulin and Mucin Domain-Containing Molecule 3 (TIM-3)," J Med Chem, 64: 14757-14772 (2021).

Sasikumar et al., "PD-1 derived CA-170 is an oral immune checkpoint inhibitor that exhibits preclinical anti-tumor efficacy," Communications Biology, 4: 12 pages (2021).

Shi et al., "The Role of PD-1 and PD-L1 in T-cell Immune Suppression in Patients with Hematological Malignancies," Journal of Hematology & Oncology, 6(74): 1-6 (2013).

Skrdla et al., "A Simple Quantitative FT-IR Approach for the Study of a Polymorphic Transformation Under Crystallization Slurry Conditions", Journal of Pharmaceutical and Biomedical Analysis, 25(5-6): 731-739 (2001).

Sureshbabu et al., "Synthesis of 1,2,4-oxadiazole-linked Orthogonally Urethane-Protected Dipeptide Mimetics," Tetrahedron Letters, 49(35): 5133-5136 (2008).

Tagliamento et al., "VISTA: A Promising Target for Cancer Immunotherapy?" Immuno Targets and Therapy, 10: 185-200 (2021).

Takada, "API form screening and selection in drug discovery stage", Pharm Stage, 6(10):20-25. (2007).

Waldmann, "Effective Cancer Therapy Through Immunomodulation," T Annu Rev Med, 57: 65-81 (2006).

Wu et al., "VISTA inhibitors in cancer immunotherapy: a short perspective on recent progresses," RSC Med Chem, 12: 1672-1679 (2021).

Golub, et al., "Molecular Classification of Cancer: Class Discovery and Class Prediction by Gene Expression Monitoring," Science, 286(5439): 531-537 (1999).

Lala et al., "Role of nitric oxide in tumor progression: lessons from experimental tumors", Cancer and Metastasis Reviews 17: 91-106 (1998).

National Institute of Health, "Cancer" Medline Plus, Retrieved from the internet, URL: https://medlineplus.gov/cancer.html. [online], [retrieved on Jun. 30, 2023].

U.S. Appl. No. 17/461,512, Pending.

Baldoni et al: "A New Reversible and Potent P2Y12 Receptor Antagonist (ACT-246475): Tolerability, Pharmacokinetics, and Pharmacodynamics in a First-in-Man Trial", Clinical Drug Investigation, Nov. 1, 2014.

Alsaab et al., "PD-1 and PD-L1 Checkpoint Signaling Inhibition for CancerImmunotherapy: Mechanism, Combinations, and Clinical Outcome" Frontiers in Pharmacology, vol. 8, No. 561 (2017).

Ansell, "PD-1 Is Expressed on B-Cells in Waldenstrom Macroglobulinemia and Promotes Malignant Cell Viability and Proliferation" Blood, vol. 124, No. 21 (2014).

Balbach et al., "Pharmaceutical evaluation of early development candidates "the 100 mg-approach"." International Journal of Pharmaceutics 275.1-2 (2004): 1-12.

Caira, "Crystalline polymorphism of organic compounds." Design of Organic Solids (1998): 163-208.

Cedres et al., "Analysis of Expression of Programmed Cell Death 1 Ligand 1 (PD-L1) in Malignant Pleural Mesothelioma (MPM)" Plos One DOI:10.1371 (2015).

Curiel et al., "Blockade of B7-H1 improves myeloid dendritic cell-mediated anitumor immunity" Nature Medicine, vol. 9, No. 5 (2003).

Singhal et al., "Drug polymorphism and dosage form design: a practical perspective." Advanced Drug Delivery Reviews 56.3 (2004): 335-347.

Swaika et al., "Current state of anti-PD-L1 and anti-PD-1 agents in cancer therapy" Molecular Immunology (2015).

U.S. Appl. No. 15/556,800, Granted.
U.S. Appl. No. 16/945,854, Granted.
U.S. Appl. No. 17/962,976, Pending.
U.S. Appl. No. 15/298,539, Granted.
U.S. Appl. No. 15/713,671, Granted.
U.S. Appl. No. 16/192,030, Granted.
U.S. Appl. No. 16/806,872, Granted.
U.S. Appl. No. 17/192,279, Granted.
U.S. Appl. No. 17/981,695, Pending.
U.S. Appl. No. 16/343,681, Pending.
U.S. Appl. No. 16/761,162, Granted.
U.S. Appl. No. 18/516,458, Pending.
U.S. Appl. No. 16/651,830, Granted.
U.S. Appl. No. 17/350,445, Granted.
U.S. Appl. No. 18/101,387, Allowed.
U.S. Appl. No. 18/414,958, Pending.
U.S. Appl. No. 16/755,439, Granted.
U.S. Appl. No. 17/461,512, Granted.
U.S. Appl. No. 16/761,964, Granted.
U.S. Appl. No. 17/960,586, Pending.

Form 1

CRYSTALLINE FORMS OF 3-SUBSTITUTED 1,2,4-OXADIAZOLE

CROSS-REFERENCE TO RELATED APPLICATION

This application is a continuation of U.S. application Ser. No. 17/461,512, filed Aug. 30, 2021, which is a continuation of U.S. application Ser. No. 16/755,439, filed Apr. 10, 2020, now U.S. Pat. No. 11,136,300, which is the § 371 National Stage of PCT/IB2018/057840, filed Oct. 10, 2018, which claims the benefit of priority to Indian Provisional Patent Application serial number 201741036169, filed Oct. 11, 2017, the contents of each of which are hereby incorporated by reference herein in their entirety.

BACKGROUND

The immune system in mammals regulates the activation and inactivation of lymphocytes through various mechanisms during and after an immune response. Among these mechanisms, there are mechanisms that specifically modulate the immune response as and when required.

3-substituted 1,2,4-oxadiazole compounds act as immunomodulators. Thus, 3-substituted 1,2,4-oxadiazole compounds can be used in the treatment of cancer, immune disorders, immunodeficiency disorders, inflammatory disorders, infectious diseases, and transplant rejection.

Given the therapeutic benefits associated with 3-substituted 1,2,4-oxadiazole compounds, there is a need for improved compositions of these compounds. Further, there is a need for improved methods for preparing and formulating 3-substituted 1,2,4-oxadiazole compounds.

SUMMARY

One aspect of the invention relates to a crystalline compound having the structure of formula (I),

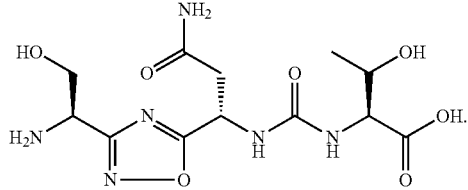

Another aspect of the invention relates to methods for preparing the crystalline compounds of formula (I).

In certain embodiments, the present invention provides a pharmaceutical preparation suitable for use in a human patient, comprising a crystalline compound of formula (I), and one or more pharmaceutically acceptable excipients. In certain embodiments, the pharmaceutical preparations may be for use in treating or preventing a condition or disease as described herein.

DETAILED DESCRIPTION

Figure 1:
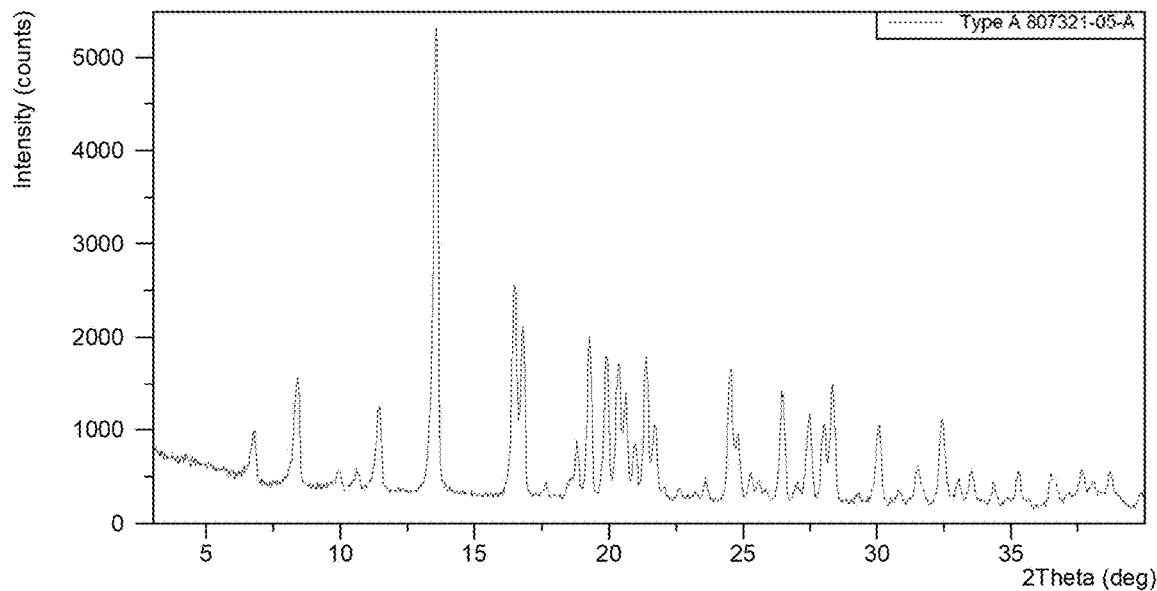
FIG. 1 shows the XRPD patterns of formula (I) Form 1.

In certain embodiments, the invention provides a crystalline compound having the structure of formula (I),

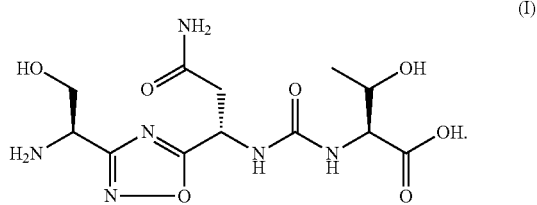 [SMILES: CC(O)[C@H](NC(=O)N[C@@H](CC(N)=O)c1nc([C@@H](N)CO)no1)C(=O)O]

In some embodiments, the invention provides a crystalline compound having the structure of formula (I) could also be written by showing all of the atoms,

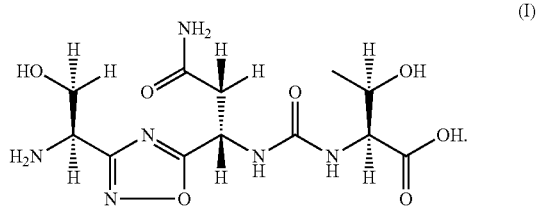

In certain embodiments, a crystalline compound of formula (I) is solvated. In certain such embodiments, the crystalline compound of formula (I) is a hydrate (e.g., a monohydrate or a dihydrate). In certain particular embodiments, the crystalline compound of formula (I) is a monohydrate. In certain particular embodiments, the crystalline compound of formula (I) is a dihydrate.

Any crystalline compound described herein may be used in the manufacture of a medicament for the treatment of any diseases or conditions disclosed herein.

In certain embodiments, the compounds of the present invention can assemble into more than one crystal formation. In an exemplary embodiment, the crystalline compound having the structure of formula (I) exists as "Form 1", "Form 2", or a mixture thereof, as described in detail below. These different forms are understood as "polymorphs" herein.

In certain embodiments, the polymorph of the crystalline compound is characterized by powder X-ray diffraction (XRD). θ represents the diffraction angle, measured in degrees. In certain embodiments, the diffractometer used in XRD measures the diffraction angle as two times the diffraction angle θ. Thus, in certain embodiments, the diffraction patterns described herein refer to X-ray intensity measured against angle 2θ.

In certain embodiments, a crystalline compound of formula (I) is solvated.

In some embodiments, a crystalline compound of formula (I) is solvated with water and is a hydrate. In certain embodiments, the crystalline hydrate of the compound of formula (I) is a monohydrate or a dihydrate. In other embodiments, the crystalline hydrate of the compound of formula (I) is a monohydrate. In other embodiments, the crystalline hydrate of the compound of formula (I) is a dihydrate.

In certain embodiments, a crystalline hydrate of the compound of formula (I) has 2θ values 8.4±0.2, 13.6±0.2, 16.5±0.2, 16.8±0.2, 21.4±0.2, and 28.4±0.2. In further embodiments, the crystalline hydrate has 2θ values 8.4±0.2, 13.6±0.2, 16.5±0.2, 16.8±0.2, 19.3±0.2, 20.4±0.2, 21.4±0.2, and 28.4±0.2. In yet further embodiments, the crystalline hydrate has 2θ values 8.4±0.2, 13.6±0.2, 16.5±0.2, 16.8±0.2, 19.3±0.2, 19.9±0.2, 20.4±0.2, 21.4±0.2, 24.5±0.2, 26.5±0.2, and 28.4±0.2. In further embodiments, the crystalline hydrate has 2θ values 8.4±0.2, 11.5±0.2, 13.6±0.2, 16.5±0.2, 16.8±0.2, 19.3±0.2, 19.9±0.2, 20.4±0.2, 21.4±0.2, 21.8±0.2, 24.5±0.2, 26.5±0.2, 27.5±0.2, 28.0±0.2, 28.4±0.2, 30.0±0.2, and 32.4±0.2. In some embodiments, the crystalline hydrate has 2θ values selected from the following peaks listed Table 1±0.2.

TABLE 1

Exemplary peaks of Form 1

| Pos. [°2Th.] | Height [cts] | FWHM Left [°2Th.] | d-spacing [Å] | Rel. Int. [%] |
|---|---|---|---|---|
| 6.818730 | 477.062400 | 0.153504 | 12.96356 | 9.84 |
| 8.429180 | 1106.154000 | 0.230256 | 10.49006 | 22.83 |
| 9.996699 | 162.963200 | 0.179088 | 8.84842 | 3.36 |
| 10.641450 | 181.680600 | 0.204672 | 8.31371 | 3.75 |
| 11.473900 | 856.673700 | 0.179088 | 7.71235 | 17.68 |
| 13.586620 | 4846.171000 | 0.179088 | 6.51746 | 100.00 |
| 16.523190 | 2235.245000 | 0.179088 | 5.36517 | 46.12 |
| 16.841620 | 1711.580000 | 0.153504 | 5.26444 | 35.32 |
| 17.642590 | 99.168370 | 0.153504 | 5.02720 | 2.05 |
| 18.833270 | 580.986700 | 0.127920 | 4.71197 | 11.99 |
| 19.308990 | 1653.407000 | 0.179088 | 4.59694 | 34.12 |
| 19.940700 | 1511.741000 | 0.153504 | 4.45272 | 31.19 |
| 20.379910 | 1426.443000 | 0.179088 | 4.35774 | 29.43 |
| 20.640480 | 1063.284000 | 0.127920 | 4.30331 | 21.94 |
| 20.981490 | 582.937600 | 0.153504 | 4.23413 | 12.03 |
| 21.395090 | 1507.023000 | 0.153504 | 4.15321 | 31.10 |
| 21.751640 | 776.502400 | 0.153504 | 4.08593 | 16.02 |
| 22.616420 | 99.647250 | 0.204672 | 3.93161 | 2.06 |
| 23.625170 | 188.599900 | 0.153504 | 3.76598 | 3.89 |
| 24.523500 | 1372.566000 | 0.179088 | 3.63002 | 28.32 |
| 24.824960 | 695.664600 | 0.102336 | 3.58662 | 14.35 |
| 25.319510 | 269.242600 | 0.179088 | 3.51768 | 5.56 |
| 26.486100 | 1097.968000 | 0.204672 | 3.36533 | 22.66 |
| 27.046260 | 201.561100 | 0.179088 | 3.29689 | 4.16 |
| 27.509350 | 900.113200 | 0.204672 | 3.24243 | 18.57 |
| 28.032180 | 818.228900 | 0.153504 | 3.18313 | 16.88 |
| 28.357680 | 1216.173000 | 0.179088 | 3.14733 | 25.10 |
| 29.284110 | 65.256650 | 0.153504 | 3.04984 | 1.35 |
| 30.078100 | 824.492300 | 0.230256 | 2.97112 | 17.01 |
| 30.808680 | 118.232400 | 0.204672 | 2.90231 | 2.44 |
| 31.530650 | 388.319600 | 0.153504 | 2.83748 | 8.01 |
| 32.440480 | 869.745500 | 0.204672 | 2.75995 | 17.95 |
| 33.044710 | 264.978200 | 0.127920 | 2.71085 | 5.47 |
| 33.486020 | 328.815100 | 0.179088 | 2.67613 | 6.79 |
| 34.329380 | 233.555300 | 0.102336 | 2.61229 | 4.82 |
| 35.275910 | 345.531500 | 0.179088 | 2.54434 | 7.13 |
| 36.461080 | 277.000200 | 0.102336 | 2.46431 | 5.72 |
| 37.629320 | 368.294900 | 0.179088 | 2.39044 | 7.60 |
| 38.089640 | 238.710400 | 0.204672 | 2.36261 | 4.93 |
| 38.729290 | 317.873000 | 0.153504 | 2.32505 | 6.56 |

In certain embodiments, a crystalline hydrate of the compound of formula (I) has an XRD pattern substantially as shown in FIG. 1, labeled Form 1.

In some embodiments, the crystalline hydrate has 2θ values 12.9±0.2, 13.5±0.2, 15.7±0.2, 17.0±0.2, 29.7±0.2, and 33.7±0.2. In further embodiments, the crystalline hydrate has 2θ values 12.9±0.2, 13.5±0.2, 15.7±0.2, 17.0±0.2, 20.3±0.2, 28.9±0.2, 29.7±0.2, and 33.7±0.2. In yet further embodiments, the crystalline hydrate has 2θ values 12.9±0.2, 13.5±0.2, 15.7±0.2, 17.0±0.2, 19.6±0.2, 20.3±0.2, 26.2±0.2, 28.9±0.2, 29.7±0.2, and 33.7±0.2. In still further embodiments, the crystalline hydrate has 2θ values 12.9±0.2, 13.5±0.2, 15.7±0.2, 17.0±0.2, 19.1±0.2, 19.6±0.2, 20.3±0.2, 21.1±0.2, 21.4±0.2, 26.2±0.2, 27.2±0.2, 28.9±0.2, 29.7±0.2, 32.2±0.2, and 33.7±0.2. In some embodiments, the crystalline hydrate has 2θ values selected from the following peaks listed Table 2±0.2.

TABLE 2

Exemplary peaks of Form 2

| Pos. [°2Th.] | Height [cts] | FWHM Left [°2Th.] | d-spacing [Å] | Rel. Int. [%] |
|---|---|---|---|---|
| 10.926180 | 397.133600 | 0.102336 | 8.09770 | 19.80 |
| 11.592880 | 174.246700 | 0.127920 | 7.63345 | 8.69 |
| 12.933320 | 570.548600 | 0.102336 | 6.84516 | 28.45 |
| 13.459840 | 2005.257000 | 0.102336 | 6.57856 | 100.00 |
| 15.662360 | 1080.314000 | 0.102336 | 5.65806 | 53.87 |
| 16.071480 | 201.940400 | 0.102336 | 5.51494 | 10.07 |
| 16.951470 | 1230.626000 | 0.127920 | 5.23057 | 61.37 |
| 19.134270 | 1076.042000 | 0.127920 | 4.63852 | 53.66 |
| 19.553070 | 1440.614000 | 0.127920 | 4.54011 | 71.84 |
| 20.306040 | 1175.604000 | 0.204672 | 4.37342 | 58.63 |
| 21.053740 | 714.116700 | 0.102336 | 4.21977 | 35.61 |
| 21.422720 | 517.599900 | 0.102336 | 4.14791 | 25.81 |
| 22.172010 | 165.219600 | 0.102336 | 4.00940 | 8.24 |
| 22.869490 | 92.001400 | 0.153504 | 3.88868 | 4.59 |
| 24.193950 | 163.135600 | 0.127920 | 3.67871 | 8.14 |
| 24.523350 | 238.576700 | 0.102336 | 3.63004 | 11.90 |
| 24.789210 | 371.732200 | 0.102336 | 3.59171 | 18.54 |
| 25.095920 | 276.245600 | 0.102336 | 3.54851 | 13.78 |
| 25.791380 | 281.323200 | 0.102336 | 3.45438 | 14.03 |
| 26.153440 | 745.307100 | 0.102336 | 3.40737 | 37.17 |
| 26.402310 | 226.278200 | 0.076752 | 3.37582 | 11.28 |
| 27.224340 | 576.143400 | 0.153504 | 3.27572 | 28.73 |
| 28.230660 | 218.307800 | 0.102336 | 3.16120 | 10.89 |
| 28.862240 | 803.457000 | 0.127920 | 3.09345 | 40.07 |
| 29.715230 | 554.454300 | 0.179088 | 3.00657 | 27.65 |
| 30.204860 | 251.635200 | 0.076752 | 2.95894 | 12.55 |
| 31.028680 | 198.270100 | 0.102336 | 2.88223 | 9.89 |
| 32.232440 | 414.918300 | 0.127920 | 2.77728 | 20.69 |
| 33.668980 | 788.804300 | 0.153504 | 2.66200 | 39.34 |
| 34.180000 | 83.372570 | 0.307008 | 2.62336 | 4.16 |
| 36.002300 | 76.087860 | 0.153504 | 2.49465 | 3.79 |
| 37.016770 | 103.663100 | 0.204672 | 2.42858 | 5.17 |
| 38.371850 | 39.207050 | 0.307008 | 2.34588 | 1.96 |
| 38.980620 | 67.341840 | 0.204672 | 2.31063 | 3.36 |

Figure 2:
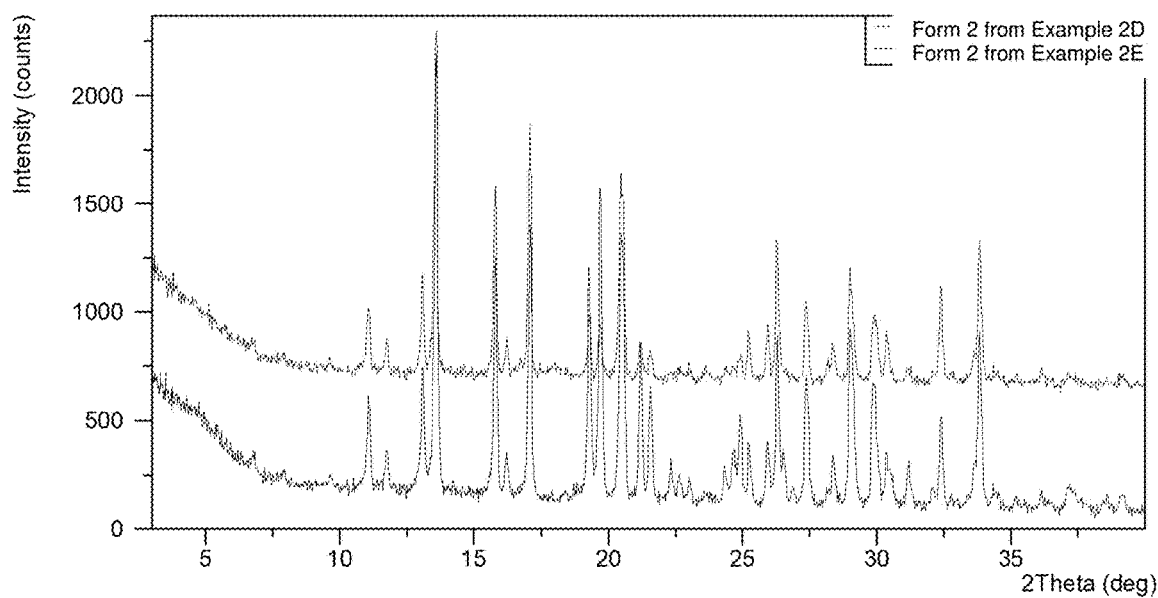
FIG. 2 shows overlay XRPD patterns of formula (I) Form 2 from example 2D and Example 2E

In certain embodiments, a crystalline hydrate of the compound of formula (I) has an XRD pattern substantially as shown in FIG. 2, labeled Form 2.

In certain embodiments, the crystalline hydrate of the compound of formula (I) is a monohydrate. In certain embodiments, the crystalline hydrate of the compound of formula (I) contains about 0.9, about 1.0, about 1.1, or about 1.2 molecules of water to one molecule of the compound of formula (I). In certain embodiments, the crystalline hydrate of the compound of formula (I) by differential scanning calorimetry (DSC) shows one or two overlapping endotheinis with a peak temperature from about 115° C. to about 145° C. before melting/decomposition. In some embodiments, the crystalline hydrate of the compound of formula (I) shows one or two overlapping endotherms with a peak temperature in the range selected from about 116° C. to about 140° C. before melting/decomposition. In some embodiments, the crystalline hydrate of the compound of formula (I) shows one or two overlapping endotherms with a peak temperature in the range selected from about 120° C. to about 140° C., about 125° C. to about 135° C., and about 126° C. to about 133° C. by DSC before melting/decomposition. See FIG. 3, labeled Form 1.

In certain embodiments, the crystalline hydrate of the compound of formula (I) is a dihydrate. In certain embodiments, the crystalline hydrate of the compound of formula (I) contains about 1.8, about 1.9, about 2.0, about 2.1, or about 2.2 molecules of water to one molecule of the compound of formula (I). In certain embodiments, the crystalline hydrate of the compound of formula (I) by differential scanning calorimetry (DSC) shows two endotherms with a peak temperature of the first endotherm in the range selected from about 25° C. to about 65° C., 30° C. to about 60° C., about 40° C. to about 55° C., and about 45° C. to about 50° C.; and a peak temperature of the second endotherm in the range selected from about 60° C. to about 85° C., about 65° C. to about 80° C., and about 70° C. to about 75° C. before melting/decomposition. See FIG. 4, labeled Form 2.

In some embodiments, the crystalline hydrate of the compound of formula (I) shows melting/decomposition with an onset temperature in the range selected from about 178° C. to about 190° C., about 182° C. to about 186° C., and about 183° C. to about 185° C. by DSC.

In certain embodiments, the invention relates to a pharmaceutical composition comprising a crystalline compound of formula (I) and one or more pharmaceutically acceptable excipients. In certain embodiments, the pharmaceutical composition is selected from tablets, capsules, and suspensions.

In certain embodiments, the pharmaceutical composition comprises the salt of the compound of formula (I) and one or more pharmaceutically acceptable excipients.

Definitions

As used in the present specification, the following words and phrases are generally intended to have the meanings as set forth below, except to the extent that the context in which they are used indicates otherwise.

As used herein, the term "hydrate" refers to a complex formed by the combining of Compound of formula (I) and water. The term includes stoichiometric as well as non-stoichiometric hydrates.

As used herein, the term "solvate" refers to a complex formed by the combining of Compound of formula (I) and a solvent.

As used herein, "therapeutically effective amount" refers to an amount that is sufficient to effect treatment, when administered to a mammal in need of such treatment. The therapeutically effective amount will vary depending upon the subject being treated, the weight and age of the subject, the severity of the disease condition, the manner of administration and the like, which can readily be determined by one of ordinary skill in the art.

The term "substantially pure", as used herein, refers to a crystalline polymorph that is greater than 90% pure, meaning that it contains less than 10% of any other compound, or an alternative polymorph of the crystalline form. Preferably, the crystalline polymorph is greater than 95% pure, or even greater than 98% pure.

The phrase "substantially as shown in Fig." refers to an X-ray powder diffraction pattern with at least 50%, or at least 60%, or at least 70%, or at least 80%, or at least 90%, or at least 95% or at least 99% of its peak appears in FIG.

As used herein, the term "about" when referring to a number or a numerical range means that the number or numerical range referred to, is an approximation within experimental variability (or within statistical experimental error), and thus the number or numerical range may vary from, for example, between 1% and 15% of the stated number or numerical range.

Methods of Making the Crystalline Forms of the Compound of Formula (I)

In certain embodiments, the invention relates to a method for preparing a crystalline compound having the structure of formula (I), comprising:
a) providing a mixture comprising a compound of formula (I) and a solvent; and
b) crystallizing the compound of formula (I) from the mixture comprising the compound of formula (I).

In certain embodiments, the mixture comprising the compound of formula (I) and the solvent is a reaction mixture.

In certain embodiments, the mixture comprising the compound of formula (I) is a solution. In certain embodiments, the solution comprises a compound of formula (I) dissolved in a solvent. In some embodiments, the solution comprises a crude solid material comprising the compound of formula (I) dissolved in a solvent. In some embodiments, the solution comprises a reaction mixture.

In certain embodiments, the mixture is a slurry or a suspension. In certain embodiments, the slurry or the suspension comprises crude solid material comprising the compound of formula (I).

In certain embodiments of the solutions, slurries, and suspensions disclosed herein, the crude solid material comprising the compound of formula (I) is less than 70% pure, less than 75% pure, less than 80% pure, less than 85% pure, or less than 90% pure with respect to the compound of formula (I). In certain embodiments, the crude solid material comprising the compound of formula (I) is less than 90% pure with respect to the compound of formula (I). In certain embodiments, the crude solid material comprises about 70% to about 90% compound of formula (I). In some embodiments, the purity of the crude solid material is about 70% to about 90% with respect to the compound of formula (I).

In certain embodiments, after crystallization, the compound of formula (I) is substantially pure. In some embodiments, the crystalline form of the compound of formula (I) is greater than 90% pure. In some embodiments, the purity of the crystalline form of the compound of formula (I) is selected from greater than 90%, greater than 91%, greater than 92%, greater than 93%, greater than 94%, greater than 95%, greater than 96%, greater than 97%, greater than 98%, and greater than 99%. In some embodiments, the purity of the crystalline form of the compound of formula (I) is greater than 95%. In some embodiments, the purity of the crystalline form of the compound of formula (I) is greater than 98%. In some embodiments, the purity of the crystalline form of the compound of formula (I) is selected from about 90%, about 91%, about 92%, about 93%, about 94%, about 95%, about 96%, about 97%, about 98%, and about 99%.

In certain embodiments, the crystalline compound made by the methods of the invention is a solvate, e.g., a hydrate.

In certain embodiments, the crystalline compound made by the methods of the invention is a monohydrate.

In certain embodiments, the crystalline compound made by the methods of the invention is a dihydrate.

In some embodiments, solvent vapor slowly diffuses into a solid sample. In some embodiments, the solvent vapor is water vapor. In some embodiments, for example to achieve Form 2, the solid sample is Form 1, and solvent is water.

In certain embodiments, the crystalline Form 1 of compound of formula (I), can be substantially free of other crystalline forms of compound of formula (I). In certain embodiments, the crystalline Form 1 of compound of formula (I), can be substantially free of crystalline Form 2 of compound of formula (I).

In certain embodiments, the crystalline Form 2 of compound of formula (I), can be substantially free of other crystalline forms of compound of formula (I). In certain embodiments, the crystalline Form 2 of compound of formula (I), can be substantially free of crystalline Form 1 of compound of formula (I).

In certain embodiments, the mixture comprising the compound of formula (I) is a solution, and the step of crystallizing the compound from the mixture comprises bringing the solution to supersaturation to cause the compound of formula (I) to precipitate out of solution.

In certain embodiments, bringing the mixture comprising the compound of formula (I) to supersaturation comprises the slow addition of an anti-solvent, such as heptanes, hexanes, ethanol, or another polar or non-polar liquid miscible with an aqueous solution, allowing the solution to cool (with or without seeding the solution), reducing the volume of the solution, or any combination thereof. In certain embodiments, the anti-solvent is ethanol, isopropanol, methanol, tetrahydrofuran, 1,4-dioxane, acetonitrile, methyl tert-butyl ether, isopropyl acetate and acetone. In certain embodiments, the anti-solvent is ethanol, isopropanol, methanol, tetrahydrofuran, 1,4-dioxane, acetonitrile and acetone. In certain embodiments, the anti-solvent is ethanol. In certain embodiments, bringing the mixture comprising the compound of formula (I) to supersaturation comprises adding an anti- solvent, cooling the solution to ambient temperature or lower, and reducing the volume of the solution, e.g., by evaporating solvent from the solution. In certain embodiments, allowing the solution to cool may be passive (e.g., allowing the solution to stand at ambient temperature) or active (e.g., cooling the solution in an ice bath or freezer).

In certain embodiments, the preparation method further comprises isolating the crystals, e.g., by filtering the crystals, by decanting fluid from the crystals, or by any other suitable separation technique. In further embodiments, the preparation method further comprises washing the crystals.

In certain embodiments, the preparation method further comprises inducing crystallization. The method can also comprise drying the crystals, for example under reduced pressure. In certain embodiments, inducing precipitation or crystallization comprises secondary nucleation, wherein nucleation occurs in the presence of seed crystals or interactions with the environment (crystallizer walls, stirring impellers, sonication, etc.).

In other embodiments, the solvent is acetonitrile, diethyl ether, N,N-dimethylacetamide (DMA), dimethylformamide (DMF), dimethylsulfoxide (DMSO), dichloromethane, ethanol, ethyl acetate, heptanes, hexanes, isopropyl acetate, methanol, methylethyl ketone, N-methyl-2-pyrrolidone (NMP), tetrahydrofuran, toluene, 2-propanol (isopropanol), 1-butanol, water, or any combination thereof. In some embodiments, the solvent is dichloromethane. In some preferred embodiments, for example to achieve Form 1, the solvent is tetrahydrofuran.

In some embodiments, the anti-solvent is selected from tetrahydrofuran, methanol, isopropanol, diethyl ether, ethanol, 1,4-dioxane, acetonitrile, and acetone. In some embodiments, to an aqueous solution comprising the compound of formula (I) is slowly added an anti-solvent. In certain preferred embodiments, for example to achieve Form 2, an aqueous solution comprising Form 1 is combined with an anti-solvent selected from tetrahydrofuran, methanol, isopropanol, diethyl ether, ethanol, 1,4-dioxane, acetonitrile, and acetone.

In some embodiments, the anti-solvent is selected from tetrahydrofuran, methanol, isopropanol, 1,4-dioxane, acetonitrile, and acetone. In some embodiments, an anti-solvent slowly diffuses into an aqueous solution comprising the compound of formula (I). In certain preferred embodiments, for example to achieve Form 2, an aqueous solution comprising Form 1 is diffused with an anti-solvent selected from tetrahydrofuran, methanol, isopropanol, 1,4-dioxane, acetonitrile, and acetone.

In some embodiments, a slurry comprising the compound of formula (I) and a solvent were mixed before isolating the solids. In some embodiments, the isolation of the solids is by filtration or centrifugation. In some embodiments, to achieve Form 2, the slurry comprising Form 1 was mixed with a solvent selected from acetonitrile, anisole, dichloromethane, ethanol, isopropyl acetate, methyl tert-butyl ether (MTBE), n-heptane, tetrahydrofuran, water, and mixtures thereof.

In some embodiments, to achieve Form 2, the slurry comprising Form 1 was mixed with a solvent selected from acetonitrile, ethanol, methyl tert-butyl ether (MTBE), water, and mixtures thereof.

In some embodiments, to achieve Form 2, the slurry comprising compound was mixed with a solvent selected from acetonitrile, methyl tert-butyl ether (MTBE), water, and mixtures thereof.

In certain embodiments, the solvent is a mixture comprising water. In some preferred embodiments, the solvent is a mixture comprising water and ethanol, isopropanol, methanol, or tetrahydrofuran. In certain preferred embodiments, for example to achieve Form 2, the solvent is a mixture comprising water and tetrahydrofuran. In other embodiments the solvent is a mixture comprising water, and other solvents selected from ethanol, isopropanol, methanol, tetrahydrofuran, 1,4-dioxane, acetonitrile, and acetone.

In certain preferred embodiments, the solvent mixture is selected from water/tetrahydrofuran ($H_2O$/THF), water/methanol ($H_2O$/MeOH), water/isopropanol ($H_2O$/IPA), water/ethanol ($H_2O$/EtOH), water/1,4-dioxane ($H_2O$/1,4-dioxane), water/acetonitrile ($H_2O$/ACN), or water/Acetone ($H_2O$/Acetone).

In some embodiments, the solvent is a mixture comprising EtOH:$H_2O$ in a volume-to-volume ratio selected from 19:2, 5:1, 2:1, 1:1, and 1:9. In some embodiments, the solvent is a mixture comprising ethanol and water to which additional ethanol or a mixture of ethanol and water is added. In some embodiments, the mixture comprises the compound of formula (I) and a solvent of 2:1 EtOH:$H_2O$ (v/v), then a mixture of 19:2 EtOH:$H_2O$ is added for crystallization.

In some embodiments, crystallization is aided by seeding or seed loading, that is adding seed crystals to the mixture. In some embodiments, the seed crystals are added at a weight percentage of the total mixture selected from about 1 wt %, about 2 wt %, about 3 wt %, about 4 wt %, about 5 wt %, about 6 wt %, about 7 wt %, about 8 wt %, about 9 wt %, and about 10 wt %. In some embodiments, the seed crystals are added at a weight percentage of the total mixture selected from about 1 wt %, about 2 wt %, about 3 wt %, about 4 wt %, about 5 wt %, and about 6 wt %. In some embodiments, the seed crystals are added at a weight percentage of the total mixture selected from 3 wt %, 4 wt %, and 5 wt %.

In some embodiments, the seed crystals are formula (I) Form 2 seed crystals. In certain embodiments, the seed crystals are milled.

In certain embodiments, washing the crystals comprises washing with a liquid selected from anti-solvent, acetonitrile, ethanol, heptanes, hexanes, methanol, tetrahydrofuran, toluene, water, or a combination thereof.

As used herein, "anti-solvent" means a solvent in which the compound crystals are insoluble, minimally soluble, or partially soluble. In practice, the addition of an anti-solvent to a solution in which the salt crystals are dissolved reduces the solubility of the salt crystals in solution, thereby stimulating precipitation of the salt. In certain embodiments, the crystals are washed with a combination of anti-solvent and the organic solvent. In certain embodiments, the anti-solvent is water, while in other embodiments it is an alkane solvent, such as hexane or pentane, or an aromatic hydrocarbon solvent, such as benzene, toluene, or xylene. In certain embodiments, the anti-solvent is methanol.

In certain embodiments, washing the crystals comprises washing the crystalline compound of formula (I) with a solvent or a mixture of one or more solvents, which are described above. In certain embodiments, the solvent or mixture of solvents is cooled prior to washing.

In certain embodiments, the methods of making the crystalline forms of the compound of formula (I) are used to remove one or more impurities from a sample of the compound of formula (I). In certain embodiments, the crystallization methods described herein are used for purifying the compound of formula (I), e.g., as a final purification step in the manufacture of the compound.

In certain embodiments, the compound of formula (I) is purified by crystallization. In some embodiments, purification of the compound of formula (I) does not use high-performance liquid chromatography (HPLC), including preparative HPLC. In some embodiments, purification of the compound of formula (I) by crystallization is scalable. Advantages of purification by crystallization include, but are not limited to, removal of soluble impurities, ease of purification process, applicability to large scale synthesis, acceptable yields, and high product purity.

In some embodiments, the crystalline formula (I) Form 2 was the form with greater stability. In some embodiments, the crystalline formula (I) Form 2 is more stable than the crystalline formula (I) Form 1 in water. In some embodiments, the temperature was below about 20° C., below about 15° C., below about 10° C., below about 5° C., or below about 0° C. In some embodiments, the temperature was about 20° C., about 15° C., about 10° C., about 5° C., or about 0° C. In some embodiments, the temperature was about 10° C., about 9° C., about 8° C., about 7° C., about 6° C., about 5° C., about 4° C., about 3° C., about 2° C., about 1° C., about 0° C., about −1° C., or about −2° C. In some embodiments, the temperature was about 10° C.

In some embodiments, the conversion to crystalline formula (I) Form 2 was complete in about 4 h, in about 8 h, in about 12 h, in about 16 h, in about 20 h, in about 1 day, in about 2 days, in about 3 days, in about 4 days, in about 5 days, in about 6 days, in about 7 days. In some embodiments, the conversion to crystalline formula (I) Form 2 was complete in about 2 h, in about 3 h, in about 4 h, in about 5 h, in about 6 h, in about 7 h, in about 8 h, in about 9 h, in about 10 h, in about 11 h, in about 12 h, in about 13 h, in about 14 h, in about 15 h, in about 16 h, in about 17 h, in about 18 h, in about 19 h, in about 20 h, in about 21 h, in about 22 h, in about 23 h, in about 24 h, in about 25 h, or in about 26 h.

Uses of Crystal Forms of the Compound of Formula (I)

The compound of formula (I) is a 3-substituted 1,2,4-oxadiazole compound having the following structure,

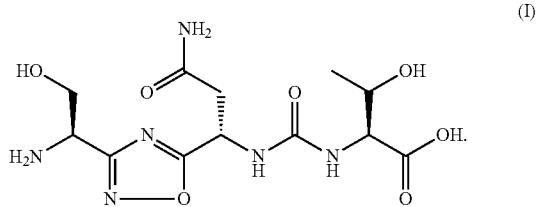 [SMILES: CC(O)[C@H](NC(=O)N[C@@H](CC(N)=O)c1nc([C@@H](N)CO)no1)C(=O)O]

Functional "exhaustion" (immune dysfunction) among T and B cell subsets is a well-described feature of chronic viral infections, such as hepatitis B and C and HIV viruses. T cell exhaustion was initially described for CD8 T cells in mice chronically infected with lymphocytic choriomeningitis virus clone 13. In the lymphocytic choriomeningitis virus mouse model, repeated antigen stimulation through the T cell antigen receptor drives the sustained expression of T cell inhibitory receptors, including programmed cell death-1 (PD-1) and lymphocyte activationgene-3 (LAG-3), on virus-specific CD8 T cells (J. Illingworth et al., J. Immunol. 2013, 190(3): 1038-1047).

Thus, diseases modulated by an immune response including, but not limited to, cancer, immune disorders, immunodeficiency disorders, inflammatory disorders, infectious diseases, and transplant rejection, can be treated by administering an immunomodulator, such as the compound of formula (I), and compositions disclosed herein. 3-substituted 1,2,4-oxadiazole compounds act as immunomodulators.

In certain embodiments, the compound of formula (I) modulates an immune response in a cell.

In other embodiments, the present disclosure provides a method of modulating an immune response in a cell, comprising contacting the cell with a composition comprising a crystalline form of the compound of formula (I), according to any of the above embodiments. In some embodiments, the present disclosure provides a method of modulating an immune response in a cell, comprising contacting the cell with a composition comprising a crystalline form of the compound of formula (I), according to any of the above embodiments.

In certain embodiments, the present disclosure provides uses of a crystalline form of the compound of formula (I) for the preparation of a medicament, e.g., for the treatment of cancer, immune disorders, immunodeficiency disorders, inflammatory disorders, infectious diseases, and transplant rejection.

In accordance with any of the foregoing embodiments, in certain embodiments, contacting the cell occurs in a subject in need thereof, thereby treating a disease or disorder selected from cancer, immune disorders, immunodeficiency disorders, inflammatory disorders, infectious diseases, and transplant rejection.

In certain embodiments, the present disclosure provides methods for treating cancer, wherein the method comprises administration of a therapeutically effective amount of a composition comprising a crystalline form of the compound of formula (I) the subject in need thereof.

In certain embodiments, the present disclosure provides methods for inhibiting growth of tumor cells and/or metastasis by administering a therapeutically effective amount of a composition comprising a crystalline form of the compound of formula (I) to the subject in need thereof.

Representative tumor cells include cells of a cancer such as, but not limited to, blastoma (e.g., glioblastoma), breast cancer (e.g., breast carcinoma, primary ductal carcinoma, triple negative breast cancer, estrogen receptor positive (ER+), progesterone receptor positive (PR+), and/or human epidermal growth factor receptor 2 positive (HER2+)), epithelial cancer (e.g., carcinomas), colon cancer, lung cancer (e.g., small cell lung cancer, non-small cell lung cancer (NSCLC), lung adenocarcinoma, and lung squamous cell carcinoma), melanoma (e.g., cutaneous melanoma, ocular melanoma, cutaneous or intraocular malignant melanoma, and lymph node-associated melanoma), prostate cancer (e.g., prostate adenocarcinoma), renal cancer (e.g., renal cell cancer (RCC) and kidney cancer), bone cancer (e.g., osteosarcoma), pancreatic cancer (e.g., pancreatic adenocarcinoma), skin cancer, cancer of the head or neck (e.g., head and neck squamous cell carcinoma), uterine cancer, ovarian cancer (e.g., ovarian carcinoma), colorectal cancer (e.g., microsatellite instability high colorectal cancer and colorectal adenocarcinoma), rectal cancer, cancer of the anal region, cancer of the peritoneum, stomach cancer (e.g., gastric carcinoma and gastrointestinal cancer), testicular cancer, carcinoma of the fallopian tubes, carcinoma of the endometrium, cervical cancer (e.g., carcinoma of the cervix), vaginal cancer (e.g., carcinoma of the vagina), vulval cancer (e.g., carcinoma of the vulva), cancer of the esophagus, cancer of the small intestine, cancer of the endocrine system, thyroid cancer (e.g., cancer of the thyroid gland), cancer of the parathyroid gland, cancer of the adrenal gland, sarcoma (e.g., sarcoma of soft tissue and Kaposi's sarcoma), cancer of the urethra, cancer of the penis, chronic or acute leukemia,(e.g., acute myeloid leukemia, chronic myeloid leukemia, acute lymphoblastic leukemia, chronic lymphocytic leukemia, Hairy cell leukemia, and chronic myeloblastic leukemia,), solid tumors of childhood, Hodgkin's lymphoma (HL) (e.g., lymphocyte-rich (LRCHL), nodular sclerosis (NSHL), mixed cellularity (MCHL) and lymphocyte depleted (LDHL)), B-cell lymphomas (e.g., diffuse large B-cell lymphoma (DLBCL)), non-Hodgkin's lymphoma (NHL) (e.g., low grade/follicular non-Hodgkin's lymphoma, small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, Burkitt's lymphoma, mantle cell lymphoma), AIDS-related lymphoma, cutaneous T-cell lymphoma (e.g., mycosis fundoides) and Waldenstrom's Macroglobulinemia, post-transplant lymphoproliferative disorder (PTLD), lymphocytic lymphoma, primary CNS lymphoma, and T-cell lymphoma), mesothelioma, thymic carcinoma, myeloma (e.g., multiple myeloma), cancer of the bladder (e.g., bladder carcinoma), cancer of the ureter, carcinoma of the renal pelvis, liver cancer (e.g., hepatocellular cancer, hepatic carcinoma, hepatoma), pancreatic cancer, post-transplant lymphoproliferative disorder (PTLD), neoplasm of the central nervous system (CNS), tumor angiogenesis, spinal axis tumor, brain stem glioma, pituitary adenoma, epidermoid cancer, salivary gland carcinoma, squamous cell cancer, abnormal vascular proliferation associated with phakomatoses, edema (such as that associated with brain tumors), Meigs' syndrome, Merkel cell carcinoma, environmentally induced cancers (including those induced by asbestos), and combinations of said cancers.

In other embodiments, for example, the tumor cells may include cells of a cancer selected from prostate cancer, melanoma, breast cancer, colon cancer, prostate cancer, lung cancer, renal cancer, pancreatic cancer, gastric carcinoma, bladder cancer, esophageal cancer, mesothelioma, thyroid cancer, thymic carcinoma, sarcoma, glioblastoma, chronic or acute leukemia, lymphoma, myeloma, Merkel cell carcinoma, epithelial cancer, colorectal cancer, vaginal cancer, cervical cancer, ovarian cancer, and cancer of the head and neck.

In other embodiments, for example, the tumor cells may include cells of a cancer selected from melanoma, triple negative breast cancer, non-small cell lung cancer, renal cell carcinoma, pancreatic cancer, gastric carcinoma, bladder cancer, mesothelioma, Hodgkins's lymphoma, cervical cancer, ovarian cancer, and head and neck squamous cell carcinoma.

In some embodiments, the tumor cells are cells of a cancer selected from small cell lung cancer, multiple myeloma, bladder carcinoma, primary ductal carcinoma, ovarian carcinoma, Hodgkin's lymphoma, gastric carcinoma, acute myeloid leukemia, and pancreatic cancer.

In other embodiments, the tumor cells are cells of a cancer selected from carcinoma of the endometrium, ovarian cancer, Hodgkin's lymphoma, non-Hodgkin's lymphoma, and chronic or acute leukemias including acute myeloid leukemia, chronic myeloid leukemia, acute lymphoblastic leukemia, chronic lymphocytic leukemia, lymphocytic lymphoma, and multiple myeloma.

In some embodiments, the tumor cells are cells of a cancer selected from prostate adenocarcinoma, lung adenocarcinoma, lung squamous cell carcinoma, pancreatic adenocarcinoma, breast cancer and colorectal adenocarcinoma. In certain embodiments, tumor cells are from breast cancer. In some embodiments, the tumor cells are from a breast cancer selected from triple negative breast cancer, estrogen receptor positive (ER+), progesterone receptor positive (PR+), and/or human epidermal growth factor receptor 2 (HER2+). In other embodiments, the tumor cells are from a PAM50+ breast cancer assay panel (Parker, J. S., et al., *J. Clin. Oncol.*, 2009, 27(8): 1160-1167), breast cancer selected from luminal A, luminal B, HER2-enriched, basal-like and normal-like.

In some embodiments, the tumor cells are cells of a cancer selected from triple negative breast cancer, microsatellite instability high colorectal cancer, gastric carcinoma, mesothelioma, pancreatic cancer, and cervical cancer.

In some embodiments, the tumor cells are, and/or the subject is, naïve to immunooncology therapy. Immunooncology uses the subject's immune system to help fight cancer. For example, an immunooncology therapy includes, but is not limited to, atezolizumab (human monoclonal antibody that targets PD-L1), avelumab (human monoclonal antibody that targets PD-L1), brentuximab vedotin (antibody-drug conjugate that targets CD30), durvalamab (human monoclonal antibody that targets PD-L1), ipilimumab (human monoclonal antibody that targets CTLA-4), nivolumab (human monoclonal antibody that targets PD-LI), pembrolizumab (also referred to as lambrolizumab, human monoclonal antibody that targets PD-L1), tremelimumab (human monoclonal antibody that targets CTLA-4), CT-011 (antibody that targets PD-1), MDX-1106 (antibody that targets PD-1), MK-3475 (antibody that targets PD-1), YW243.55.S70 (antibody that targets PD-L1), MPDL3280A(antibody that targets PD-L1), MDX-1105 (antibody that targets PD-L1), and MEDI4736 (antibody that targets PD-L1). In some embodiments, the immunooncology therapy is selected from an anti-CTLA-4 antibody, an anti-PD-1 antibody, an anti-PD-L1 antibody, an anti-PD-L2 antibody, an anti-TIGIT antibody (e.g., antibodies disclosed in WO 2015/009856).

In other embodiments, the tumor cells are, and/or the subject is responsive to immune checkpoint therapy. In some embodiments, the cancer has shown response to anti- PD1 therapy. For example, the cancer may include non-small cell lung cancer (NSCLC), melanoma, renal cell cancer (RCC), cancer of the bladder, Hodgkin's lymphoma, and head and neck squamous cell carcinoma.

Other embodiments of the present disclosure provide a method of treatment of infection.

Still other embodiments of the present disclosure provide a method of treatment of infection comprising administration of a therapeutically effective amount of a composition comprising a crystalline form of the compound of formula (I) to the subject in need thereof.

In certain embodiments, the present disclosure provides uses of a crystalline form of the compound of formula (I) for the preparation of a medicament for the treatment of infectious disease, as well as methods of administering a therapeutically effective amount of a composition comprising a crystalline form of the compound of formula (I) for the treatment of infectious disease.

In some embodiments, the infectious disease is bacterial infection, viral infection, fungal infection, or parasitic infection, as well as methods of administering a therapeutically effective amount of a composition comprising a crystalline form of the compound of formula (I) for the treatment of bacterial infection, viral infection, fungal infection, or parasitic infection.

In some embodiments, for example, bacterial infection may be caused by at least one bacterium selected from anthrax, *Bacilli, Bordetella, Borrelia,* botulism, *Brucella, Burkholderia, Campylobacter, Chlamydia,* cholera, *Clostridium, Conococcus, Corynebacterium,* diptheria, *Enterobacter, Enterococcus, Erwinia, Escherichia, Francisella, Haemophilus, Heliobacter, Klebsiella, Legionella, Leptospira,* leptospirosis, *Listeria,* Lyme's disease, *Meningococcus, Mycobacterium, Mycoplasma, Neisseria, Pasteurella, Pelobacter,* plague, *Pneumonococcus, Proteus,*

*Pseudomonas, Rickettsia, Salmonella, Serratia, Shigella, Staphylococcus, Streptococcus,* tetanus, *Treponema, Vibrio, Yersinia* and *Xanthomonas*.

In other embodiments, for example, viral infection may be caused by at least one virus selected from Adenoviridae, Papillomaviridae, Polyomaviridae, Herpesviridae, Poxviridae, Hepadnaviridae, Parvoviridae, Astroviridae, Caliciviridae, Picornaviridae, Coronoviridae, Flaviviridae, Retroviridae, Togaviridae, Arenaviridae, Bunyaviridae, Filoviridae, Orthomyxoviridae, Paramyxoviridae, Rhabdoviridae, and Reoviridae. In certain embodiments, the virus may be arboviral encephalitis virus, adenovirus, herpes simplex type I, herpes simplex type 2, Varicella-zoster virus, Epstein-barr virus, cytomegalovirus, herpesvirus type 8, papillomavirus, BK virus, coronavirus, echovirus, JC virus, smallpox, Hepatitis B, bocavirus, parvovirus B19, astrovirus, Norwalk virus, coxsackievirus, Hepatitis A, poliovirus, rhinovirus, severe acute respiratory syndrome virus, Hepatitis C, yellow fever, dengue virus, West Nile virus, rubella, Hepatitis E, human immunodeficiency virus (HIV), human T-cell lymphotropic virus (HTLV), influenza, guanarito virus, Junin virus, Lassa virus, Machupo virus, Sabia virus, Crimean-Congo hemorrhagic fever virus, ebola virus, Marburg virus, measles virus, molluscum virus, mumps virus, parainfluenza, respiratory syncytial virus, human metapneumovirus, Hendra virus, Nipah virus, rabies, Hepatitis D, rotavirus, orbivirus, coltivirus, vaccinia virus, and Banna virus.

In other embodiments, for example, fungal infection may be selected from thrush, *Aspergillus* (*fumigatus, niger,* etc.), *Blastomyces dermatitidis, Candida* (*albicans, krusei, glabrata, tropicalis,* etc.), *Coccidioides immitis, Cryptococcus* (*neoformans,* etc.), *Histoplasma capsulatum, Mucorales* (*mucor, absidia, rhizophus*), *Paracoccidioides brasiliensis,* sporotrichosis, *Sporothrix schenkii,* zygomycosis, chromoblastomycosis, lobomycosis, mycetoma, onychomycosis, piedra pityriasis versicolor, tinea barbae, tinea capitis, tinea corporis, tinea cruris, tinea favosa, tinea nigra, tinea pedis, otomycosis, phaeohyphomycosis, and rhinosporidiosis.

In some embodiments, for example, parasitic infection may be caused by at least one parasite selected from *Acanthamoeba, Babesia microti, Balantidium coli, Entamoeba hystolytica, Giardia lamblia, Cryptosporidium muris, Trypanosomatida gambiense, Trypanosomatida rhodesiense, Trypanosoma brucei, Trypanosoma cruzi, Leishmania mexicana, Leishmania braziliensis, Leishmania tropica, Leishmania donovani, Toxoplasma gondii, Plasmodium vivax, Plasmodium ovale, Plasmodium malariae, Plasmodium falciparum, Pneumocystis carinii, Trichomonas vaginalis, Histomonas meleagridis, Secementea, Trichuris trichiura, Ascaris lumbricoides, Enterobius vermicularis, Ancylostoma duodenale, Naegleria fowleri, Necator americanus, Nippostrongylus brasiliensis, Strongyloides stercoralis, Wuchereria bancrofti, Dracunculus medinensis,* blood flukes, liver flukes, intestinal flukes, lung flukes, *Schistosoma mansoni, Schistosoma haematobium, Schistosoma japonicum, Fasciola hepatica, Fasciola gigantica, Heterophyes heterophyes,* and *Paragonimus westermani*.

The term "subject" includes mammals (especially humans) and other animals, such as domestic animals (e.g., household pets including cats and dogs) and non-domestic animals (such as wildlife).

As used herein, a therapeutic that "prevents" a disorder or condition refers to a compound that, in a statistical sample, reduces the occurrence or frequency of the disorder or condition in the treated sample relative to an untreated control sample, or delays the onset or reduces the severity of one or more symptoms of the disorder or condition relative to the untreated control sample. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof).

Pharmaceutical Compositions

In certain embodiments, the present disclosure provides a pharmaceutical composition comprising a crystalline form of the compound of formula (I) as disclosed herein, optionally admixed with a pharmaceutically acceptable carrier or diluent.

The present disclosure also provides methods for formulating the disclosed crystalline forms of the compound of formula (I) for pharmaceutical administration.

The compositions and methods of the present disclosure may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a crystalline form of the compound of formula (I) of the disclosure and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a crystalline form of the compound of formula (I) of the disclosure. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a self-emulsifying drug delivery system or a self-microemulsifying drug delivery system. The pharmaceutical composition (preparation) also can be a liposome or other polymer matrix, which can have incorporated therein, for example, a crystalline form of the compound of formula (I) of the disclosure. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a crystalline form of the compound of formula (I) of the disclosure, with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this disclosure. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference in its entirety. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

A suppository also is contemplated as being within the scope of this disclosure.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this disclosure, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the crystalline form of the compound of formula (I) of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present disclosure, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The invention now being generally described, it will be more readily understood by reference to the following examples which are included merely for purposes of illustration of certain aspects and embodiments of the present invention, and are not intended to limit the invention.

EXAMPLES

Analytical Methods

X-Ray Powder Diffraction

X-Ray Powder Diffraction patterns were collected on an Empyrean diffractometer or an X'Pert3 diffractometer using Cu Kα radiation (45 kV, 40 mA).

The details of the data collection are summarized in Table 3:

TABLE 3

| X-Ray Powder Diffraction Parameters | | | |
|---|---|---|---|
| Instrument | PANalytical | | |
| Model | Empyrean (Reflection Mode) | X' Pert3 (Reflection Mode) | Empyrean (Transmission Mode) |
| X-Ray wavelength | Cu, kα, Kα1 (Å): 1.540598, Kα2 (Å): 1.544426 Kα2/Kα1 intensity ratio: 0.50 | | |
| X-Ray tube setting | 45 kV, 40 mA | | |
| Divergence slit | Automatic | Fixed 1/8° | Fixed 1/2° |
| Scan mode | Continuous | | |
| Scan range (°2TH) | 3°-40° | | |
| Scan step time [s] | 17.8 | 46.7 | 33.02 |
| Step size (°2TH) | 0.0167 | 0.0263 | 0.0167 |
| Test Time (s) | 5 min 30 s | 5 min 04 s | 10 min 11 s |

HPLC

Purity analysis was performed on an Agilent HP1100 series system equipped with a diode array detector and using ChemStation software vB.04.03 using the method detailed below in Table 4.

TABLE 4

| HPLC Parameters | |
|---|---|
| Parameter | Value |
| Type of method | Reversed phase with gradient elution |
| Sample Preparation | Diluent, acetonitrile/$H_2O$ = 1:1 |
| Column | ZIC-HILIC, 250 × 4.6 mm, 5 μm |
| Column Temperature | 30° C. |
| Injection Volume | 10 μL |
| Detector Wavelength, Bandwidth | UV at 210 nm |
| Flow Rate | 1.0 mL/min |
| Mobile Phase A | 10 mM $KH_2PO_4$ in $H_2O$ |
| Mobile Phase B | acetonitrile |
| Gradient Timetable | Time (min)  % Mobile Phase A |
| | 0.0  80 |
| | 2.0  80 |
| | 20.0  60 |
| | 20.1  80 |
| | 30.0  80 |

Thermogravimetric Analysis and Differential Scanning Calorimetry

Thermogravimetric analysis (TGA) data were collected using a TA Q500/Q5000 TGA from TA Instruments. Differential scanning calorimetry (DSC) was performed using a TA Q200/Q2000 DSC from TA Instruments. Method parameters are provided in Table 5 below.

TABLE 5

| TGA and DSC Parameters | | |
|---|---|---|
| Parameters | TGA | DSC |
| Method | Ramp | Ramp |
| Pan | Platinum, open | Aluminum plate, crimped |
| Temperature | RT-Target Temperature | 25° C.-Target Temperature |
| Ramp rate | 10° C./min | 10° C./min |
| Purge gas | $N_2$ | $N_2$ |

PXRD Determination of Formula (I) as Reported in WO 2015/033299

Figure 8:
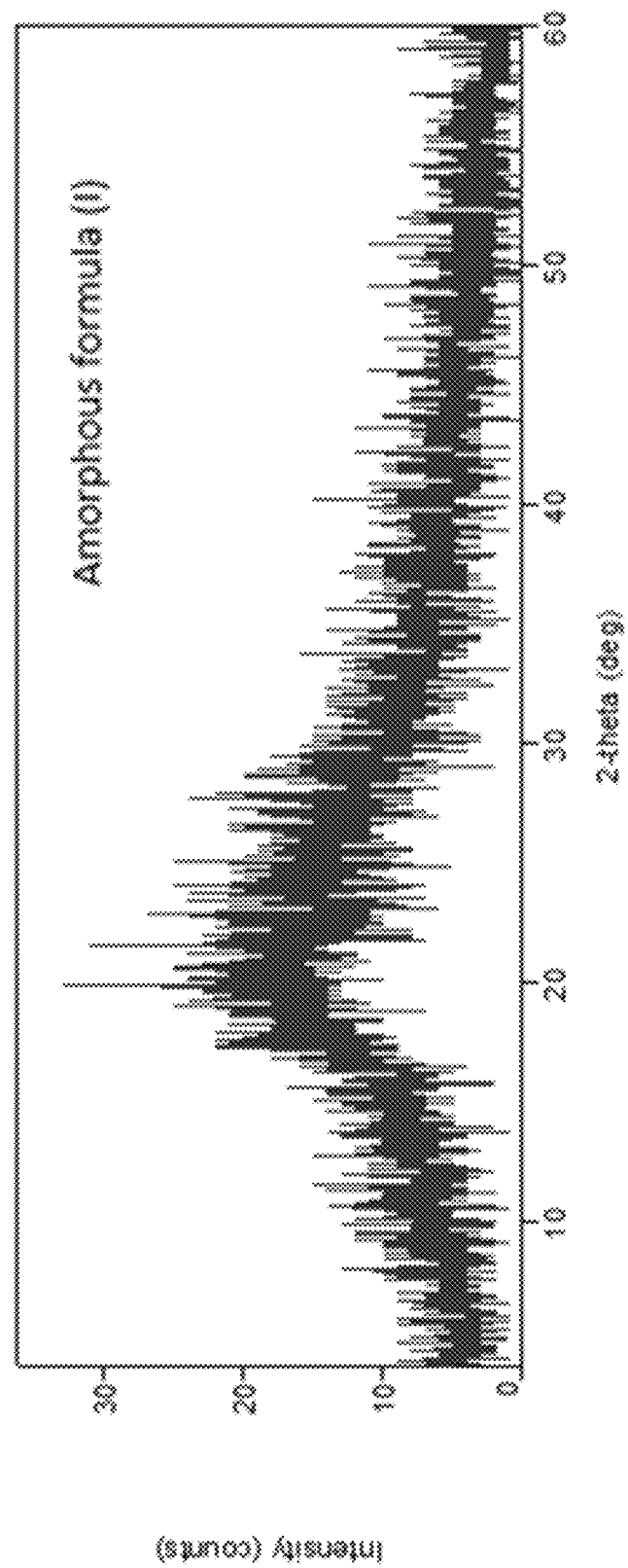
FIG. 8 shows the XRPD patterns of amorphous formula (I).

The PXRD determination of the compound of Formula (I) was obtained using the procedure described in Example 4 of WO 2015/033299, which depicts the compound to be amorphous. The PXRD is shown in FIG. 8. The contents of WO 2015/033299 are hereby incorporated by reference in their entirety.

Example 1: Synthesis of Form 1

A. Crystallization from Tetrahydrofuran

Formula (I) Form 1 exists at ambient conditions upon short term storage (i.e., less than 8 d). A mixture of formula (I) Forms 1 and 2 (16 mg) was weighed into a glass vial, and tetrahydrofuran (THF, 0.5 mL) was added. The resulting slurry was stirred at room temperature for about 4 d. The wet solids were analyzed by XRPD in transmission mode and confirmed to be crystalline formula (I) Form 1, as shown by XRPD analysis (FIG. 1).

B. Crystallization from an Ethanol/Water Mixture

About 68.0 g of amorphous compound of formula (I) was dissolved in a minimum amount of water, and ethanol was added to the solution to obtain a white precipitate. The solid was isolated by filtration. The solid was washed with ethanol followed by a wash with diethyl ether. The solid was dried under high vacuum and confirmed to be formula (I) Form 1 by XRPD analysis.

Example 2: Synthesis of Form 2

A. Solid Vapor Diffusion

Formula (I) Form 1 (approximately 15.3 mg) was weighed into a 3-mL vial, which was then placed into a 20-mL vial with 4.0 mL of water. The 20-mL vial was sealed with a cap and kept at RT for a week allowing solvent vapor to interact with the sample. The obtained solid was shown by XRPD analysis to be crystalline formula (I) Form 2.

B. Anti-Solvent Addition

About 15.0 mg of formula (I) Form 1 sample was dissolved in 0.3 mL of $H_2O$ in a 20-mL glass vial and stirred at RT. The corresponding anti-solvent (e.g., THF, MeOH, IPA, EtOH, 1,4-dioxane, ACN or Acetone) was added to the above aqueous solution till precipitate appeared or the total volume reached 15.0 mL The solids were isolated by centrifugation and confirmed to be formula (I) Form 2 by XRPD analysis.

TABLE 6

Exemplary Solvent Systems to Synthesize Formula (I) Form 2 by Anti-Solvent Addition

| No. | Methods | Solvent System |
|---|---|---|
| 1 | Anti-solvent addition | $H_2O$/THF |
| 2 | | $H_2O$/MeOH |
| 3 | | $H_2O$/IPA |
| 4 | | $H_2O$/EtOH |
| 5 | | $H_2O$/1,4-dioxane |
| 6 | | $H_2O$/ACN |
| 7 | | $H_2O$/Acetone |

C. Solution Vapor Diffusion

About 15.0 mg of formula (I) Form 1 was dissolved in 0.3 mL of $H_2O$ in a 3-mL glass vial at RT. The clear solutions in uncapped, open vials were then placed into a 20-mL vial with 4.0 mL of the anti-solvent (e.g., THF, MeOH, IPA, EtOH, 1,4-dioxane, ACN or Acetone). The 20-mL vial was sealed with a cap and kept at RT allowing interaction between vapor and the solution. The solids were confirmed to be formula (I) Form 2 by XRPD analysis.

TABLE 7

Exemplary Solvent Systems to Synthesize Formula (I) Form 2 by Vapor Diffusion

| No. | Methods | Solvent System |
|---|---|---|
| 1 | Solution vapor diffusion | $H_2O$/THF |
| 2 | | $H_2O$/MeOH |
| 3 | | $H_2O$/IPA |
| 4 | | $H_2O$/ACN |
| 5 | | $H_2O$/1,4-dioxane |
| 6 | | $H_2O$/acetone |

D. Slurry

About 20.0 mg of formula (I) Form 1 was weighed into a glass vial, and 0.5 mL of corresponding solvent (as shown in Table 8) was added. After slurry at the assigned temperature (mentioned below in Table 6) for about 3 days, the solids were isolated by centrifugation and confirmed to be formula (I) Form 2 by XRPD analysis (FIG. 2)

TABLE 8

Exemplary Solvent Systems to Synthesize Formula (I) Form 2 by Slurry

| No. | Methods | Solvent System, v:v |
|---|---|---|
| 1 | Slurry at RT | EtOH |
| 2 | | Anisole |
| 3 | | MTBE |
| 4 | | n-heptane |
| 5 | | DCM |
| 6 | | EtOH/$H_2O$, 97:3, $a_w$ = 0.2 |
| 7 | | EtOH/$H_2O$, 92.7:7.3, $a_w$ = 0.4 |
| 8 | | EtOH/$H_2O$, 86:14, $a_w$ = 0.6 |
| 9 | | EtOH/$H_2O$, 71:29, $a_w$ = 0.8 |

TABLE 8-continued

Exemplary Solvent Systems to Synthesize Formula (I) Form 2 by Slurry

| No. | Methods | Solvent System, v:v |
|---|---|---|
| 10 | | ACN/MTBE, 1:1 |
| 11 | Slurry at 50° C. | EtOH |
| 12 | | IPAc |
| 13 | | THF/IPAc, 1:1 | v:v = vol./vol;
aw = water activity at 25° C.

E. Anti-Solvent Addition Using Water/Acetonitrile Mixture

The compound was dissolved in one volume of water and added 10 vol. of acetonitrile to that and stirred for 12 hrs. The white solid was precipitated out. The precipate was filtered and washed with 1% $H_2O$ in Acetonitrile (2 vol) and washed with Acetonitrile (2 vol). The precipitate was finally washed with MTBE (10 vol) and dried under high vacuum for 10-15 h. The solids were confirmed to be formula (I) Form 2 by XRPD analysis (FIG. 2).

F. Liquid Vapor Diffusion

About 15.0 mg of formula (I) Form 1 was weighed into a 3 mL glass vial with the addition of 0.3 mL $H_2O$ (solvent). After vortexing, the suspension was filtered by Polytetrafluoroethylene (PTFE) filtering membrane, and the solution was transferred to a new 3 mL glass vial. Then the uncapped, open vial was placed in a 20 mL glass vial with 4 mL of 1,4-dioxane (anti-solvent), and the system was kept at room temperature for liquid vapor diffusion. After 70 days at room temperature, rod-like crystals suitable for single crystal X-ray diffraction were obtained.

Example 3: Thermogravimetric Analysis and Differential Scanning Calorimetry of Formula (I)

Figure 3:
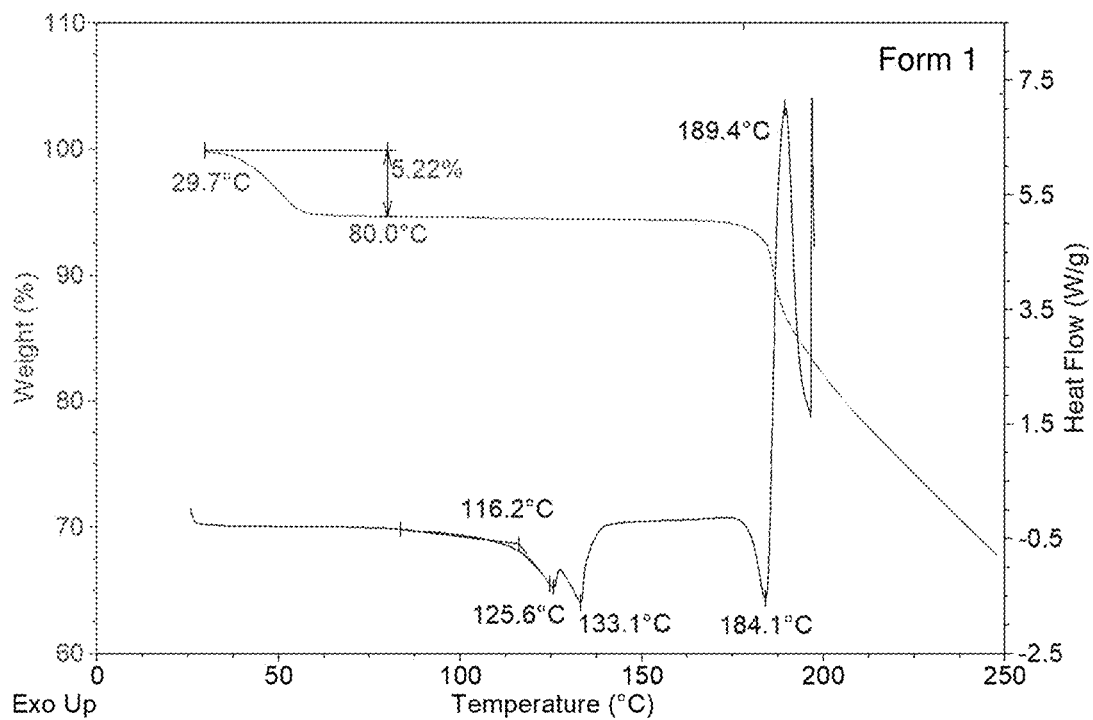
FIG. 3 shows the thermogravimetric analysis and differential scanning calorimetry thermogram of Form 1.

Thermogravimetric analysis (TGA) of formula (I) Form 1 showed a weight loss of 5.2% up to 80° C., which is consistent with a monohydrate form. Differential scanning calorimetry (DSC) showed two overlapped endotherms at 125.6° C. and 133.1° C. (peak temperature) before melting/decomposition with an onset at 184.1° C. (FIG. 3).

Figure 4:
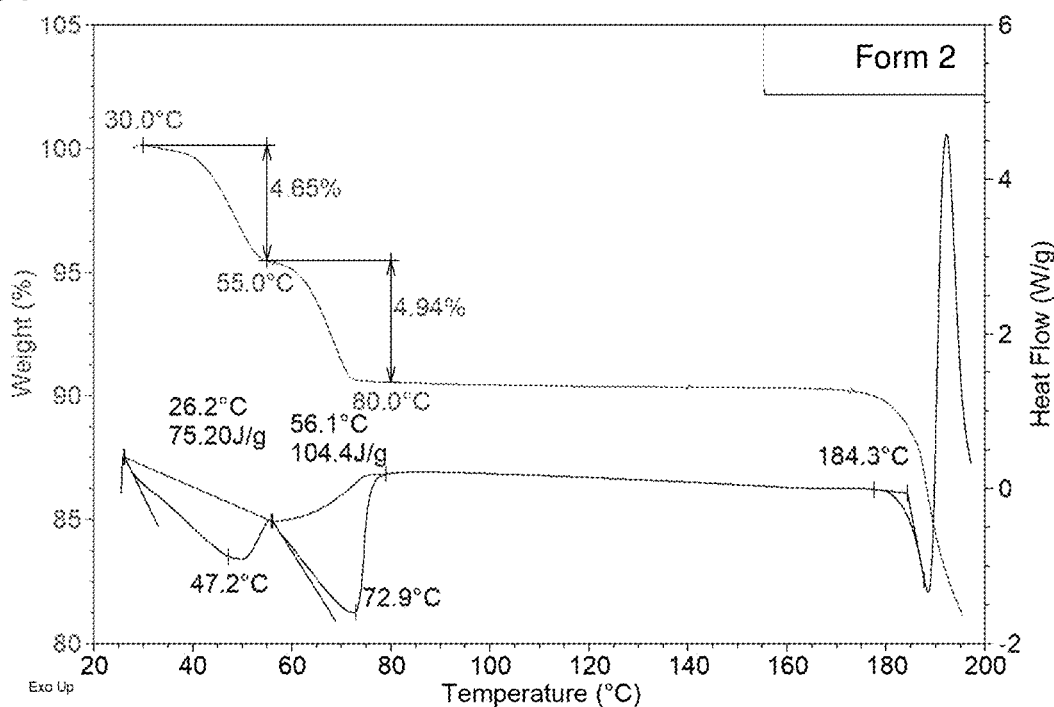
FIG. 4 shows the thermogravimetric analysis and differential scanning calorimetry thermogram of Form 2.

TGA of formula (I) Form 2 showed a two-step weight loss of 9.6% up to 80° C., which is consistent with a dihydrate form. DSC showed two endotherms at 47.2° C. and 72.9° C. (peak temperature) before melting/decomposition with an onset at 184.3° C. (FIG. 4).

Example 4: Stability and Forced Degradation Study for Crystalline Formula (I)

Solid Stability

Samples of formula (I) crystalline Form 2 were stored as solids at 25° C./60% Relative Humidity (RH), 30° C./~56%, and 40° C./75% RH for 7-8 days. The samples were prepared in duplicate with an offset of 2 weeks. Each replicate was stored in a different container.

Figure 5:
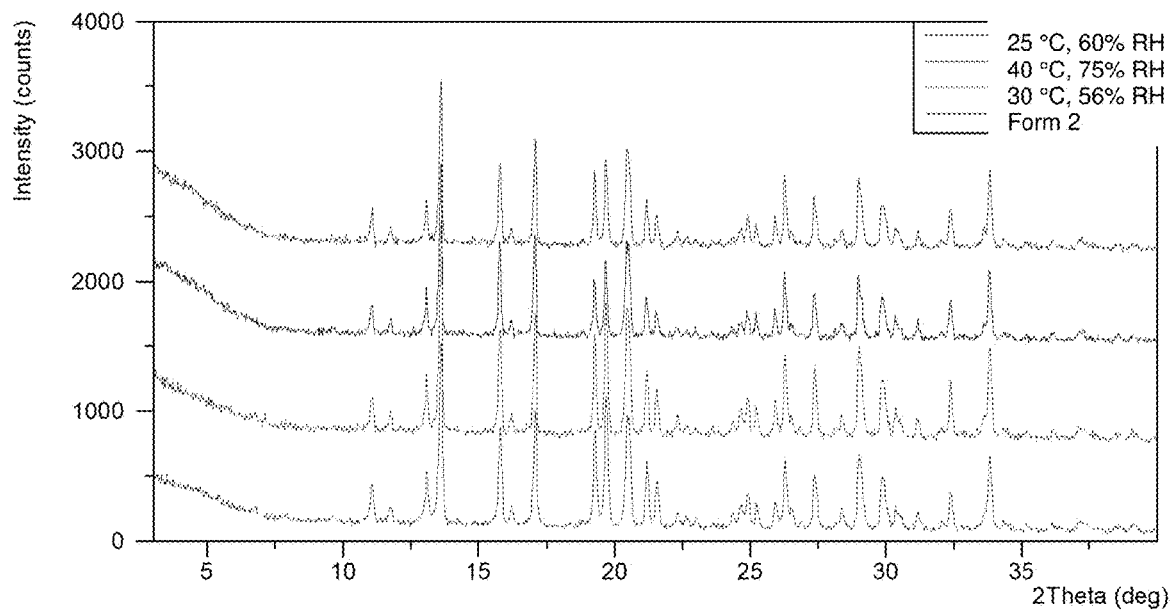
FIG. 5 shows a comparison of XRPD patterns of formula (I) Form 2 at 25° C., 60% relative humidity (RH); 40° C., 75% RH; and 30° C., 56% RH after 7-8 days compared to a Form 2 reference sample in solid form.

Formula (I) crystalline Form 2 remained unchanged in terms of solid form and particle morphology after storage for 7-8 days at 25° C./60% RH, 30° C./~56% RH, and 40° C./75% RH. See FIG. 5.

Example 5: Solubility Measurement for Crystalline Formula (I)

Equilibrium solubility of formula (I) Form 2 was measured in the water at 20° C. and 30° C. All samples were equilibrated at temperature for 6 hrs, and the solubility of supernatant was measured by HPLC, while the solids were checked by XRPD. (See Table 9.)

TABLE 9

Equilibrium Solubility of Crystal Form 2 of Formula (I)

| Starting Form | Solvent | Temp. (° C.) | Final Form | Solubility (mg/mL) |
|---|---|---|---|---|
| Form 2 | Water | 20 | Form 2 | 147.7 |
| Form 2 | | 30 | Form 2 | 165.5 |

Figure 6:
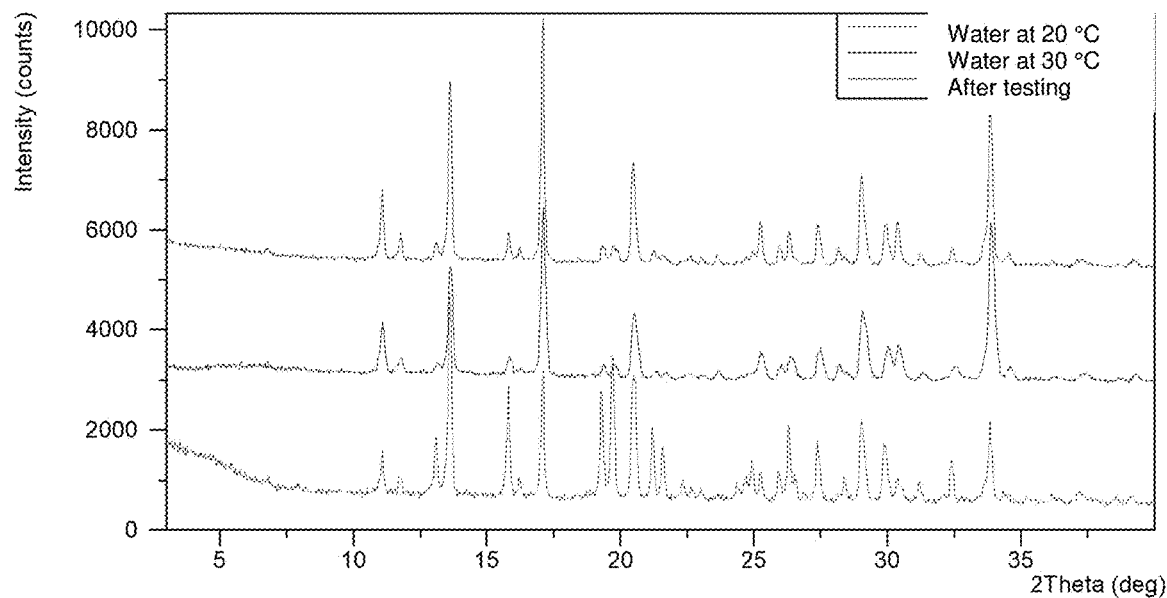
FIG. 6 shows a comparison of XRPD patterns of formula (I) Form 2 in water at 20° C.; in water at 30° C.; and Form 2 after solubility testing.

No form change was observed during the solubility testing for Form 2 (FIG. 6).

Example 6: Single Crystal Structure Determination

A single crystal for X-ray diffraction was obtained via a liquid vapor diffusion method from $H_2O$/1,4-dioxane as described in Example 2F. X-ray diffraction data was collected using a PANalytical instrument. The structural information and refinement parameters are given in Table 10.

TABLE 10

| Structural Information and Refinement Parameters for Crystal Form 2 of Formula (I) | |
|---|---|
| Empirical formula | $C_{12}H_{24}N_6O_9$ |
| Temperature | 396.37 K |
| Wavelength | Cu/Kα (λ = 1.54178 Å) |
| Crystal system, space group | Orthorhombic, $P2_12_12_1$ |
| Unit cell dimensions | a = 4.8968(2) Å α = 90° |
| | b = 15.8532(8) Å β = 90° |
| | c = 22.3708(11) Å γ = 90° |
| Volume | 1736.64(14) Å$^3$ |
| Z, Calculated density | 4, 1.516 g/cm$^3$ |
| 2 Theta range for data collection | 6.834 to 136.702° |
| Reflections collected/Independent reflections | 20428/3176 [R(int) = 0.1237] |
| Completeness | 99.97% |
| Data/restraints/parameters | 3176/0/321 |
| Goodness-of-fit on F$^2$ | 1.034 |
| Final R indices [I > 2sigma(I)] | $R_1$ = 0.0429, $wR_2$ = 0.1052 |
| Largest diff. peak and hole | 0.29/−0.33 e · Å$^{-3}$ |
| Flack parameter | 0.10(17) |

Figure 7A:
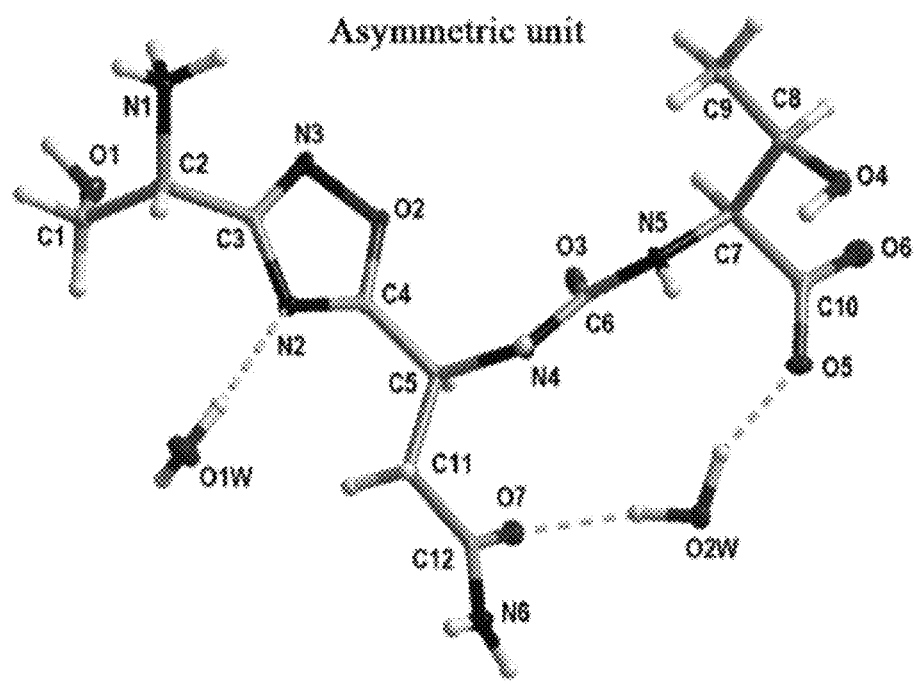
FIG. 7A shows the asymmetric unit of the formula (I) Form 2 single crystal.
Figure 7B:
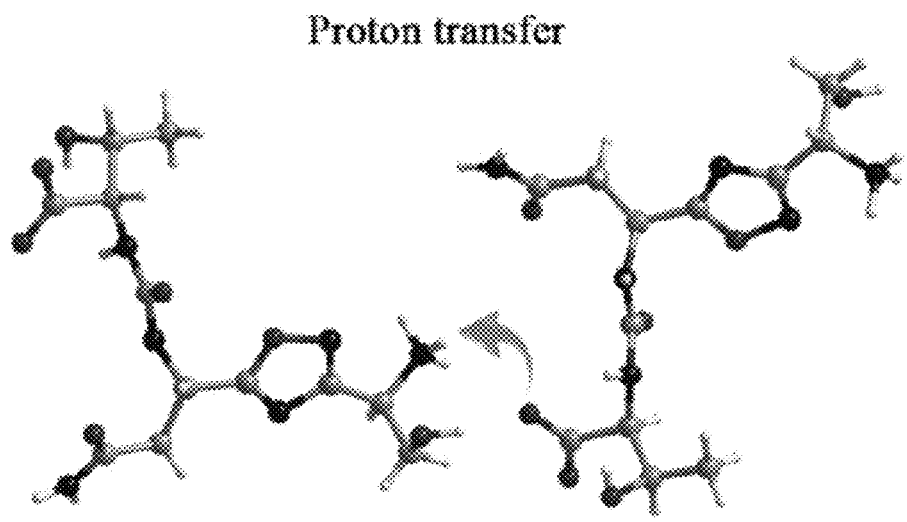
FIG. 7B shows a proposed proton transfer to form a zwitterion in the formula (I) Form 2 crystal.

Single crystal structural analysis confirmed that the crystalline formula (I) Form 2 is a dihydrate with the asymmetric unit comprised of one formula (I) molecule and two water molecules (FIG. 7A). One water molecule forms two hydrogen bonds intramolecularly with two oxygen atoms (O5 and O7) on one formula (I) molecule and intermolecularly forms two hydrogen bonds with each N1 atom on two different formula (I) molecules. This water molecule bridges the negatively and positively charged groups of the zwitterion. Two additional water molecules form an intermolecular bridge between two N2 atoms. The bond lengths of the C—O/C=O from the carboxyl group were similar. There were three residual electron density peaks assigned as the hydrogen atoms around the N1 atom. Therefore, it is suggested that the formula (I) molecule was a zwitterion in the Form 2 crystal (FIG. 7B).

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A method for preparing a crystalline compound, comprising the steps of:
   a) providing a mixture comprising the crystalline compound and a first solvent;
   b) crystallizing the compound from the mixture by:
      i) contacting the mixture with an anti-solvent; or
      ii) heating the mixture for a period of time; and
   wherein the crystalline compound and the compound have the structure of formula (I):

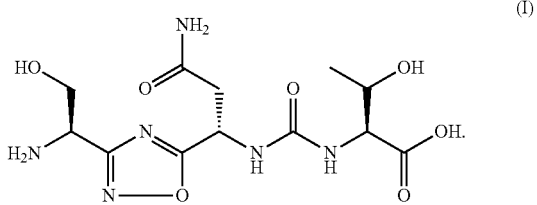 [SMILES: CC(O)[C@H](NC(=O)N[C@@H](CC(N)=O)c1nc([C@@H](N)CO)no1)C(=O)O]

2. The method of claim 1, wherein the crystalline compound is solvated.

3. The method of claim 1, wherein the crystalline compound is a hydrate.

4. The method of claim 1, wherein the crystalline compound is a monohydrate.

5. The method of claim 4, wherein the crystalline compound has 2θ values 8.4±0.2, 13.6±0.2, 16.5±0.2, 16.8±0.2, 21.4±0.2, and 28.4±0.2.

6. The method of claim 4, wherein the crystalline compound has 2θ values 8.4±0.2, 13.6±0.2, 16.5±0.2, 16.8±0.2, 19.3±0.2, 20.4±0.2, 21.4±0.2, and 28.4±0.2.

7. The method of claim 4, wherein the crystalline compound has 2θ values 8.4±0.2, 13.6±0.2, 16.5±0.2, 16.8±0.2, 19.3±0.2, 19.9±0.2, 20.4±0.2, 21.4±0.2, 24.5±0.2, 26.5±0.2, and 28.4±0.2.

8. The method of claim 4, wherein the crystalline compound has 2θ values 8.4±0.2, 11.5±0.2, 13.6±0.2, 16.5±0.2, 16.8±0.2, 19.3±0.2, 19.9±0.2, 20.4±0.2, 21.4±0.2, 21.8±0.2, 24.5±0.2, 26.5±0.2, 27.5±0.2, 28.0±0.2, 28.4±0.2, 30.0±0.2, and 32.4±0.2.

9. The method of claim 4, wherein the crystalline compound has 2θ values of 6.8±0.2, 8.4±0.2, 10.0±0.2, 10.6±0.2, 11.5±0.2, 13.6±0.2, 16.5±0.2, 16.8±0.2, 17.6±0.2, 18.8±0.2, 19.3±0.2, 19.9±0.2, 20.4±0.2, 20.6±0.2, 21.00±0.2, 21.4±0.2, 21.8±0.2, 22.6±0.2, 23.6±0.2, 24.5±0.2, 24.8±0.2, 25.3±0.2, 26.5±0.2, 27.1±0.2, 27.5±0.2, 28.0±0.2, 28.4±0.2, 29.3±0.2, 30.1±0.2, 30.8±0.2, 31.5±0.2, 32.4±0.2, 33.0±0.2, 33.5±0.2, 34.3±0.2, 35.3±0.2, 36.5±0.2, 37.6±0.2, 38.1±0.2, and 38.7±0.2.

10. The method of claim 4, wherein the crystalline compound has an XRD pattern substantially as shown in FIG. 1.

11. The method of claim 1, wherein the compound is a dihydrate.

12. The method of claim 11, wherein the crystalline compound has 2θ values 12.9±0.2, 13.5±0.2, 15.7±0.2, 17.0±0.2, 29.7±0.2, and 33.7±0.2.

13. The method of claim 11, wherein the crystalline compound has 2θ values 12.9±0.2, 13.5±0.2, 15.7±0.2, 17.0±0.2, 20.3±0.2, 28.9±0.2, 29.7±0.2, and 33.7±0.2.

14. The crystalline compound of claim 11, wherein the crystalline compound has 2θ values 12.9±0.2, 13.5±0.2, 15.7±0.2, 17.0±0.2, 19.6±0.2, 20.3±0.2, 26.2±0.2, 28.9±0.2, 29.7±0.2, and 33.7±0.2.

15. The method of claim 11, wherein the crystalline compound has 2θ values 12.9±0.2, 13.5±0.2, 15.7±0.2, 17.0±0.2, 19.1±0.2, 19.6±0.2, 20.3±0.2, 21.1±0.2, 21.4±0.2, 26.2±0.2, 27.2±0.2, 28.9±0.2, 29.7±0.2, 32.2±0.2, and 33.7±0.2.

16. The method of claim 11, wherein the crystalline compound has 2θ values of 10.9±0.2, 11.6±0.2, 12.9±0.2, 13.5±0.2, 15.7±0.2, 16.1±0.2, 17.0±0.2, 19.1±0.2, 19.6±0.2, 20.3±0.2, 21.1±0.2, 21.4±0.2, 22.2±0.2, 22.9±0.2, 24.2±0.2, 24.5±0.2, 24.8±0.2, 25.1±0.2, 25.8±0.2, 26.2±0.2, 26.4±0.2, 27.2±0.2, 28.2±0.2, 28.9±0.2, 29.7±0.2, 30.2±0.2, 31.0±0.2, 32.2±0.2, 33.7±0.2, 34.2±0.2, 36.0±0.2, 37.0±0.2, 38.4±0.2, and 39.0±0.2.

17. The method of claim 11, wherein the crystalline compound has an XRD pattern substantially as shown in FIG. 2.

18. The method of claim 1, wherein step b) comprises contacting the mixture with an anti-solvent.

19. The method of claim 18, wherein the first solvent is selected from acetonitrile, anisole, dichloromethane, ethanol, isopropyl acetate, methyl tert-butyl ether (MTBE), n-heptane, tetrahydrofuran, water, and mixtures thereof.

20. The method of claim 18, wherein the first solvent is selected from acetonitrile, ethanol, methyl tert-butyl ether (MTBE), water, and mixtures thereof.

21. The method of claim 18, wherein the first solvent is a mixture comprising water.

22. The method of claim 18, wherein the antisolvent is selected from THF, methanol, isopropyl alcohol, ethanol, 1,4-dioxane, acetonitrile or acetone.

23. The method of claim 18, wherein the antisolvent is acetonitrile.

24. The method of claim 1, wherein step b) comprises heating the mixture for a period of time.

25. The method of claim 24, wherein the first solvent is selected from acetonitrile, anisole, dichloromethane, ethanol, isopropyl acetate, methyl tert-butyl ether (MTBE), n-heptane, tetrahydrofuran, water, and mixtures thereof.

26. The method of claim 24, wherein the first solvent is selected from acetonitrile, ethanol, methyl tert-butyl ether (MTBE), water, and mixtures thereof.

27. The method of claim 24, wherein the first solvent is a mixture comprising water.

28. The method of claim 1, wherein the mixture is heated to room temperature.

29. The method of claim 1, wherein the mixture is heated to 50° C.

30. The method of claim 1, wherein the period of time is about 3 days.

31. The method of claim 28, wherein the period of time is about 3 days.

32. The method of claim 29, wherein the period of time is about 3 days.

* * * * *